United States Patent [19]

Lee et al.

[11] Patent Number: 6,048,964
[45] Date of Patent: Apr. 11, 2000

[54] COMPOSITIONS AND THERAPEUTIC METHODS USING MORPHOGENIC PROTEINS AND STIMULATORY FACTORS

[75] Inventors: John C. Lee; Lee-Chuan C. Yeh, both of San Antonio, Tex.

[73] Assignee: Stryker Corporation, Kalamazoo, Mich.

[21] Appl. No.: 08/570,752

[22] Filed: Dec. 12, 1995

[51] Int. Cl.[7] .......................... A61K 38/18; A61L 27/00; C12P 21/02; C12N 7/00

[52] U.S. Cl. .............................. 530/350; 530/300; 514/2; 435/69.1; 435/235.1; 435/240.2; 435/252.3; 435/320.1; 536/23.1

[58] Field of Search ................................ 435/69.1, 320.1, 435/235.1, 252.3, 240.2; 530/300, 350; 514/2; 536/23.1

[56] References Cited

U.S. PATENT DOCUMENTS

| | | | |
|---|---|---|---|
| 5,011,691 | 4/1991 | Oppermann et al. | 424/423 |
| 5,108,753 | 4/1992 | Kuberasampath et al. | 424/422 |
| 5,162,114 | 11/1992 | Kuberasampath et al. | 424/423 |
| 5,171,574 | 12/1992 | Kuberasampath et al. | 424/423 |
| 5,258,494 | 11/1993 | Oppermann et al. | 530/326 |
| 5,324,819 | 6/1994 | Oppermann et al. | 530/350 |
| 5,344,654 | 9/1994 | Rueger et al. | 424/423 |
| 5,354,557 | 10/1994 | Oppermann et al. | 424/423 |
| 5,459,047 | 10/1995 | Wozney et al. | 435/69.1 |
| 5,461,034 | 10/1995 | Rodan et al. | 514/14 |

FOREIGN PATENT DOCUMENTS

| | | |
|---|---|---|
| 0 514 720 | 11/1992 | European Pat. Off. . |
| 9048738 | 2/1997 | Japan . |
| WO 92/09697 | 6/1992 | WIPO . |
| WO 92/21365 | 12/1992 | WIPO . |
| WO 93/05823 | 4/1993 | WIPO . |
| 95/05846 | 3/1995 | WIPO . |
| 95/16034 | 6/1995 | WIPO . |
| 95/16035 | 6/1995 | WIPO . |
| 95/24210 | 9/1995 | WIPO . |

OTHER PUBLICATIONS

Andrews, P. W. et al., "Inhibition of Proliferation and Induction of Differentiation of Pluripotent Human Embryonal Carcinoma Cells by Osteogenic Protein–1 (Or Bone Morphogenetic Protein–7)," *Laboratory Investigation* 71:243–251 (1994).
Benayahu, D., et al., "Differential Effects of Retinoic Acid and Growth Factors on Osteoblastic Markers and CD10/NEP Activity in Stromal–Derived Osteoblasts," *Journal of Cellular Biochemistry* 56:62–72 (1994).
Benayahu, D., et al., "PTH and 1.25(OH) Vitamin D Priming To Growth Factors Differentially Regulates The Osteoblastic Markers in MBA–15 Clonal Subpopulations," *Biochemical and Biophysical Research Communications* 210:197–204 (May 5, 1995).
Canalis, Ernesto, et al., "Bone Morphogenetic Protein 2 Increases Insulin–like Growth Factor I and II Transcripts and Polypeptide Levels in Bone Cell Cultures," *Journal of Bone and Mineral Research* 9:1999–2005 (1994).

Chen, P. et al., "Osteogenic Protein–1 Promotes Growth and Maturation of Chick Sternal Chondrocytes in Serum–free Cultures, Osteogenic protein–1 promotes growth and maturation of chick sternal chondrocytes in serum–free cultures," *Journal of Cell Science* 108:105–114 (Jan. 1995).
Cook, Stephen D., et al., "Recombinant Human Bone Morphogenetic Protein–7 Induces Healing in a Canine Long–Bone Segmental Defect Model," *Clinical Orthopaedics & Related Research* 201:302–312 (Apr. 1994).
Cook, Stephen D., et al., "The Effect of Recombinant Human Osteogenic Protein–1 on Healing of Large Segmental Bone Defects," *The Journal of Bone and Joint Surgery* 76–A:827–838 (Jun. 1994).
Cook, Stephen D., et al., "In Vivo Evaluation of Recombinant Human Osteogenic Protein (rhOP–1) Implants as a Bone Graft Substitute for Spinal Fusions," *Spine* 19:1655–63 (Aug. 1, 1994).
Cook, Stephen D., et al., "Effect of Recombinant Human Osteogenic Protein–1 on Healing of Segmental Defects in Non–Human Primates," *The Journal of Bone and Joint Surgery* 77–A:734–750 (May 1995).
Dudley, A.T. et al., "A Requirement for Bone Morphogenetic Protein–7 During Development of the Mammalian Kidney and Eye," *Genes and Development* 9:2795–2807 (Nov. 1995).
Gabbitas, Bari, et al., "Bone Morphogenetic Protien–2 Inhibits the Synthesis of Insulin–Like Growth Factor–Binding Protein–5 in Bone Cell Cultures," *The Endocrine Society* 136:2397–2403 (1995).
Gitelman, Stephen E., et al., "Recombinant Vgr–1/BMP–6–expressing Tumors Induce Fibrosis and Endochondral Bone Formation In Vivo," *J. Cell Biol.* 126:1595–1609 (1994).

(List continued on next page.)

*Primary Examiner*—Nathan M. Nutter
*Attorney, Agent, or Firm*—Fish & Neave; James F. Haley, Jr.; Barbara A. Ruskin

[57] ABSTRACT

The present invention provides pharmaceutical compositions comprising a morphogenic protein stimulatory factor (MPSF) for improving the tissue inductive activity of morphogenic proteins, particularly those belonging to the BMP protein family. Methods for improving the tissue inductive activity of a morphogenic protein in a mammal using those compositions are provided. This invention also provides implantable morphogenic devices comprising a morphogenic protein and a MPSF disposed within a carrier, that are capable of inducing tissue formation in allogeneic and xenogeneic implants. Methods for inducing local tissue formation from a progenitor cell in a mammal using those devices are also provided. A method for accelerating allograft repair in a mammal using morphogenic devices is provided. This invention also provides a prosthetic device comprising a prosthesis coated with a morphogenic protein and a MPSF, and a method for promoting in vivo integration of an implantable prosthetic device to enhance the bond strength between the prosthesis and the existing target tissue at the joining site. Methods of treating tissue degenerative conditions in a mammal using the pharmaceutical compositions are also provided.

21 Claims, 12 Drawing Sheets

OTHER PUBLICATIONS

Guerne, Pierre–André, et al., "Growth Factor Responsiveness of Human Articular Chondrocytes: Distinct Profiles in Primary Chondrocytes, Subcultured Chondrocytes, and Fibroblasts," *J. Cell. Phys. 158*:476–484 (1994).

Hammerman, Marc R., "Growth Factors in Renal Development," *Seminars in Nephrology 15*:291–299 (Jul. 1995).

Helder, M.N., et al., "Expression Pattern of Osteogenic Protein–1 (Bone Morphogeneic Protein–7) in Human and Mouse Development," *J. Histochem. and Cytochem. 43*:1035–44 (Oct. 1995).

Hentunen, T.A. et al., "Effects of Recombinant Human Osteogenic Protein–1 on the Differentiation of Osteoclast- -like Cells and Bone Resorption," *Biochemical and Biophysical Research Communications 209*:433–443 (Apr. 17, 1995).

Hiraki, Yuji, et al., "Bone Morphogenetic Proteins (BMP–2 and BMP–3) Promote Growth and Expression of the Differentiated Phenotype of Rabbit Chondrocytes and Osteoblastic MC3T3–E1 Cells In Vitro," *Journal of Bone and Mineral Research 6*:1373–1385 (Dec. 1991).

Kawamura, Morio, et al., "Growth Factors, Mitogens, Cytokines, and Bone Morphogenetic Protein in Induced Chondrogenesis in Tissue Culture," *Developmental Biology 130*:435–442 (1988).

Kirker–Head, C.A., et al., "Recombinant Bone Morphogenetic Proteins: Novel Substances for Enhancing Bone Healing," *Veterinary Surgery 24*:408–418 (Sep.–Oct. 1995).

Knutsen, R., et al., "Osteogenic Protein–1 Stimulates Proliferation and Differentiation of Human Bone Cells in Vitro," *Biochemical and Biophysical Research Communications 194*:1352–1358 (Aug. 16, 1993).

Knutsen, R., et al., "Regulation of Insulin–Like Growth Factor System Components by Osteogenic Protein–1 in Human Bone Cells," *Endocrinology 136*:857–865 (Mar. 1995).

Liem, Karel, Jr., et al., "Dorsal Differentiation of Neural Plate Cells Induced by BMP–Mediated Signals from Epidermal Ectoderm," *Cell 82*:969–979 (Sep. 22, 1995).

Luo, G., et al., "BMP–7 (OP–1) Deficient Mice Fail To Develop Glomeruli And Have Skeletal Patterning Defect," *J. Bone Min. Res. 10*:97 (Aug. 1995).

Luo, G., et al., "BMP–7 is an Inducer of nephrogenesis, and is also required for eye development and skeletal patterning," *Genes & Development 9*:2808–2820 (1995).

Lyons, K.M., et al, "Colocalization of BMP 7 and BMP 2 RNAs Suggests that These Cofactors Cooperatively Mediate Tissue Interactions During Murine Development," *Mech. of Development 50*:71–83 (Mar. 1995).

Mehler, Mark F., et al., "Cytokines Regulate The Cellular Phenotype Of Developing Neural Lineage Species," *Int. J. Devel. Neuroscience 13*:213–240 (1995).

Ripamonti, U. and S. Vukicevic, "Bone Morphogenetic Proteins: From Developmental Biology to Molecular Therapeutics," *So. Afr. J. Sci. 91*:277–80 (Jun. 1995).

Rutherford, R.B., et al., "Use of Bovine Osteogenic Protein to Promote Rapid Osseointegration of Endosseous Dental Implants," *Int. J. Oral Maxilllofac. Implants 7*:297–301 (1992).

Sampath, T. K. and A.H. Reddi, "Dissociative extraction and reconstitution of extracellular matrix components involved in local bone differentiation," *Proc. Natl. Acad. Sci.—Cell Biology 78*:7599–7603 (Dec. 1981).

Sampath, T. Kuber, et al., "Recombinant Human Osteogenic Protein–1 (hOP–1) Induces New Bone Formation In Vivo with a Specific Activity Comparable with Natural Bovine Osteogenic Protein and Stimulates Osteoblast Proliferation and Differentiation in Vitro," *J. Biol. Chem. 267*:20352–20362 (Oct. 5, 1992).

Sampath, T. Kuber, et al., "Role Of Osteogenic Protein–1 (OP–1) In Growth, Development And Repair Of Bone," *J. Cellular Biochem. Supplemental 17E*:147 (1993).

Vukicevic, S., et al., "Localization of Osteogenic Protein–1 (Bone Morphogenetic Protein–7) During Human Embryonic Development: High Affinity Binding To Basement Membranes," *Biochemical and Biophysical Research Communications 198*:693–700 (Jan. 28, 1994).

Vukicevic, S., et al., "Discovery and Clinical Applications of Bone Morphogenetic Proteins," *Eur. J. Clin. Chem. Clin. Biochem. 33*:661–671 (Oct. 1995).

Wozney, John M., "The Potential Role of Bone Morphogenetic Proteins in Periodontal Reconstruction," *J. Periodontol. 66*:506–510 (1995).

COMPOSITIONS AND THERAPEUTIC METHODS USING MORPHOGENIC PROTEINS AND STIMULATORY FACTORS

BACKGROUND OF THE INVENTION

Osteogenic proteins were defined originally as an activity present in mammalian bone extracts, presumably active during growth and natural bone healing, capable of inducing a developmental cascade leading to cartilage and endochondral bone accumulation when implanted in vivo. This developmental cascade includes mesenchymal cell recruitment and proliferation, progenitor cell differentiation, cartilage calcification, vascular invasion, bone formation, remodeling and marrow differentiation (Reddi, *Collagen Rel. Res.*, 1, pp. 209–26 (1981)).

The factors in bone matrix that induce endochondral bone differentiation can be dissociatively extracted and reconstituted with inactive collagenous matrix to restore full bone inductive activity (Reddi, *Proc. Natl. Acad. Sci. USA*, 78, pp. 7599–7603 (1981)). This provides an experimental method for assaying protein extracts for their ability to induce endochondral bone formation in vivo. Using this reconstitution assay, a variety of related osteogenic proteins have been isolated from several mammalian species that are capable of inducing bone and cartilage formation in cross-species implants (Sampath and Reddi, *Proc. Natl. Acad. Sci. USA*, 80, pp. 6591–95 (1983)). The active factor or factors that promote this activity have been referred to in the literature most commonly as bone morphogenetic proteins (BMPs) and osteogenic proteins (OPs).

Osteogenic and bone morphogenetic proteins represent a family of structurally and functionally related morphogenic proteins belonging to the Transforming Growth Factor-Beta (TGF-β) superfamily (see below). The TGF-β superfamily, in turn, represents a large number of evolutionarily conserved proteins with diverse activities involved in growth, differentiation and tissue morphogenesis and repair. BMPs and osteogenic proteins, as members of the TGF-β superfamily, are expressed as secretory polypeptide precursors which share a highly conserved bioactive cysteine domain located near their C-termini. Another feature of many of the BMP family proteins is their propensity to form homo- and heterodimers.

Many morphogenic proteins belonging to the BMP family have now been described. Some have been isolated using purification techniques coupled with bioassays such as the one described above. Others have been identified and cloned by virtue of DNA sequence homologies within conserved regions that are common to the BMP family. These homologs are referred to as consecutively-numbered BMPs whether or not they have demonstrable osteogenic activity. Using an alternative approach, synthetic OPs having osteogenic activity have been designed using amino acid consensus sequences derived from sequence comparisons between naturally-derived OPs and BMPs (see below; Oppermann et al., U.S. Pat. No. 5,324,819).

While several of the earliest members of the BMP family were osteogenic proteins identified by virtue of their ability to induce new cartilage and bone, the search for BMP-related genes and gene products in a variety of species has revealed new morphogenic proteins, some of which have different or additional tissue-inductive capabilities. For example, BMP-12 and BMP-13 (identified by DNA sequence homology) reportedly induce tendon/ligament-like tissue formation in vivo (WO 95/16035). Several BMPs can induce neuronal cell proliferation and promote axon regeneration (WO 95/05846). And some BMPs that were originally isolated on the basis of their osteogenic activity also have neural inductive properties (Liem et al., *Cell*, 82, pp. 969–79 (1995)). It thus appears that osteogenic proteins and other BMPs may have a variety of potential tissue inductive capabilities whose final expression may depend on a complex set of developmental and environmental cues. These osteogenic, BMP and BMP-related proteins are referred to herein collectively as morphogenic proteins.

The activities described above, and other as yet undiscovered tissue inductive properties of the morphogenic proteins belonging to the BMP family are expected to be useful for promoting tissue regeneration in patients with traumas caused, for example, by injuries or degenerative disorders. Implantable osteogenic devices comprising mammalian osteogenic protein for promoting bone healing and regeneration have been described (see, e.g., Oppermann et al., U.S. Pat. No. 5,354,557). Some osteogenic devices comprise osteogenic protein dispersed in porous, biocompatible matrices. These naturally-derived or synthetic matrices typically allow osteogenic protein to diffuse out of the matrix into the implantation site and permit influx and efflux of cells. Osteogenic protein induces the progenitor cells to differentiate and proliferate. Progenitor cells may migrate into the matrix and differentiated cells can move out of the porous matrix into the implant site. Osteogenic cells may also utilize the matrix as a physical scaffold for osteoconduction. Similar devices have been described for delivering BMPs for tendon/ligament-like and neural tissue regeneration (see below). Osteogenic protein-coated prosthetic devices which enhance the bond strength between the prosthesis and existing bone have also been described (Rueger et al., U.S. Pat. No. 5,344,654, incorporated herein by reference).

The availability of large amounts of purified and highly active morphogenic proteins would revolutionize orthopedic medicine, certain types of plastic surgery, dental and various periodontal and craniofacial reconstructive procedures, and procedures generally involving bone, cartilage, tendon, ligament and neural regeneration. Many of the mammalian OP- and BMP-encoding genes are now cloned and may be recombinantly expressed as active homo- and heterodimeric proteins in a variety of host systems, including bacteria. The ability to recombinantly produce active forms of morphogenic proteins such as OPs and BMPs, including variants and mutants with increased bioactivities (see below), make potential therapeutic treatments using morphogenic proteins feasible.

Given the large number of potential therapeutic uses for morphogenic proteins in treating a variety of different tissues and tissue-types, there is a need for highly active forms of morphogenic proteins. It would thus be desirable to increase the tissue inductive properties of morphogenic proteins. With increased tissue inductive activity, treatment with a morphogenic protein, even on large scales, could induce tissue formation more rapidly, or tissue induction could be achieved using reduced morphogenic protein concentrations.

SUMMARY OF THE INVENTION

The present invention solves these problems by providing pharmaceutical compositions comprising a morphogenic protein stimulatory factor (MPSF) for improving the tissue inductive activity of a morphogenic protein, particularly one belonging to the BMP protein family such as osteogenic protein. Methods for improving the tissue inductive activity of a morphogenic protein in a mammal using those compositions are provided. This invention also provides implantable morphogenic devices, comprising a morphogenic protein and a MPSF disposed within a carrier, that are capable of inducing tissue formation in allogeneic and xenogeneic implants. Methods for inducing local tissue formation from a progenitor cell in a mammal using those compositions and devices are also provided. A method for accelerating allograft repair in a mammal using those morphogenic devices is provided. This invention also provides a prosthetic device comprising a prosthesis coated with a morphogenic protein and a MPSF, and a method for promoting in vivo integration of an implantable prosthetic device to enhance the bond strength between the prosthesis and the existing target tissue at the joining site. Methods for treating tissue degenerative conditions in a mammal using the pharmaceutical compositions are also provided.

DETAILED DESCRIPTION OF THE INVENTION

Figure 1:
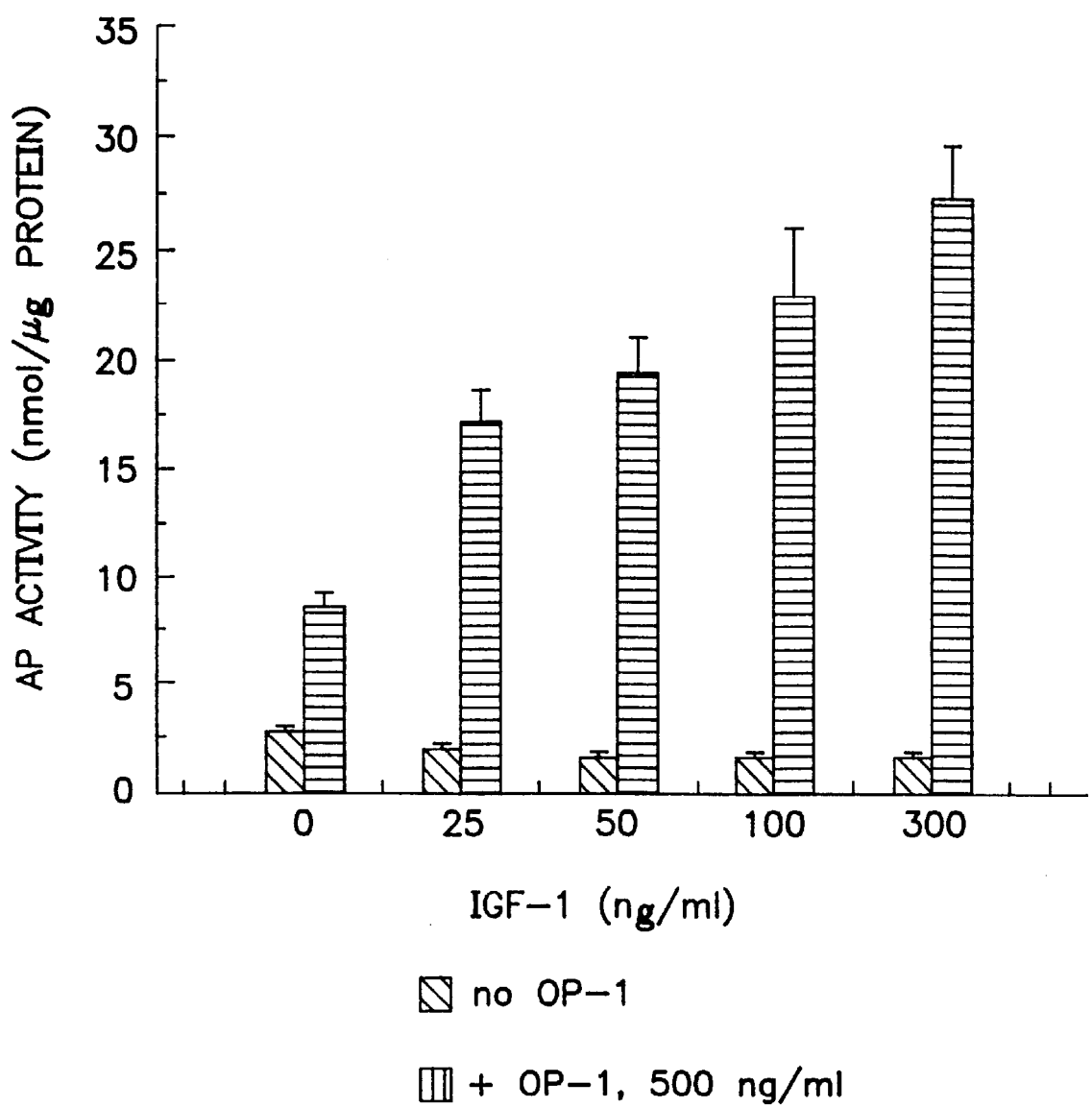
FIG. 1. IGF-I is a MPSF that stimulates OP-1 osteogenic induction. Alkaline phosphatase (AP) activity (nmol/$\mu$g protein) in FRC cells is plotted as a function of increasing IGF-I concentrations (ng/ml) in the presence or absence of OP-1 (500 ng/ml).

In order that the invention herein described may be fully understood, the following detailed description is set forth.

The term "biocompatible" refers to a material that does not elicit detrimental effects associated with the body's various protective systems, such as cell and humoral-associated immune responses, e.g., inflammatory responses and foreign body fibrotic responses. The term biocompatible also implies that no specific undesirable cytotoxic or systemic effects are caused by the material when it is implanted into the patient.

The term "bone morphogenetic protein (BMP)" refers to a protein belonging to the BMP family of the TGF-$\beta$ superfamily of proteins (BMP family) based on DNA and amino acid sequence homology. A protein belongs to the BMP family according to this invention when it has at least 50% amino acid sequence identity with at least one known BMP family member within the conserved C-terminal cysteine-rich domain which characterizes the BMP protein family. Members of the BMP family may have less than 50% DNA or amino acid sequence identity overall.

The term "morphogenic protein" refers to a protein having morphogenic activity (see below). Preferably a morphogenic protein of this invention comprises at least one polypeptide belonging to the BMP protein family. Morphogenic proteins may be capable of inducing progenitor cells to proliferate and/or to initiate differentiation pathways that lead to cartilage, bone, tendon, ligament, neural or other types of tissue formation depending on local environmental cues, and thus morphogenic proteins may behave differently in different surroundings. For example, an osteogenic protein may induce bone tissue at one treatment site and neural tissue at a different treatment site.

The term "osteogenic protein (OP)" refers to a morphogenic protein that is capable of inducing a progenitor cell to form cartilage and/or bone. The bone may be intramembranous bone or endochondral bone. Most osteogenic proteins are members of the BMP protein family and are thus also BMPs. However, the converse may not be true. BMPs (identified by sequence homology) must have demonstrable osteogenic activity in a functional bioassay to be osteogenic proteins according to this invention.

The term "morphogenic protein stimulatory factor (MPSF)" refers to a factor that is capable of stimulating the ability of a morphogenic protein to induce tissue formation from a progenitor cell. The MPSF may have a direct or indirect effect on enhancing morphogenic protein inducing activity. For example, the MPSF may increase the bioactivity of another MPSF. Agents that increase MPSF bioactivity include, for example, those that increase the synthesis, half-life, reactivity with other biomolecules such as binding proteins and receptors, or the bioavailability of the MPSF.

The terms "morphogenic activity", "inducing activity" and "tissue inductive activity" alternatively refer to the ability of an agent to stimulate a target cell to undergo one or more cell divisions (proliferation) that may optionally lead to cell differentiation. Such target cells are referred to generically herein as progenitor cells. Cell proliferation is typically characterized by changes in cell cycle regulation and may be detected by a number of means which include measuring DNA synthetic or cellular growth rates. Early stages of cell differentiation are typically characterized by changes in gene expression patterns relative to those of the progenitor cell, which may be indicative of a commitment towards a particular cell fate or cell type. Later stages of cell differentiation may be characterized by changes in gene expression patterns, cell physiology and morphology. Any reproducible change in gene expression, cell physiology or morphology may be used to assess the initiation and extent of cell differentiation induced by a morphogenic protein.

The term "synergistic interaction" refers to an interaction in which the combined effect of two agents is greater than the algebraic sum of each of their individual effects.

Morphogenic proteins

The morphogenic proteins of this invention are capable of stimulating a progenitor cell to undergo cell division and differentiation, and that inductive activity may be enhanced in the presence of a MPSF. Many mammalian morphogenic proteins have been described. Some fall within a class of products called "homeodomain proteins", named for their homology to the drosophila homeobox genes involved in phenotypic expression and identity of body segments during embryogenesis. Other morphogenic proteins are classified as peptide growth factors, which have effects on cell proliferation, cell differentiation, or both.

Peptide growth factors may be grouped into a number of superfamilies or families based primarily on their sequence similarity (Mercola and Stiles, *Development*, 102, pp. 461–60 (1988)). These families include: Epidermal Growth Factor (e.g., EGF, TGF-α, notch and delta), Transforming Growth Factor-Beta (e.g., TGF-β, inhibin, activin, MIS, BMP, dpp and Vg-1); Heparin Binding Growth Factor (e.g., FGF, ECDGF and int-2); Platelet Derived Growth Factor; Insulin-like Growth Factor (IGF-I, IGF-II); and Nerve Growth Factor.

The BMP Family

The morphogenic proteins of this invention whose activity may be enhanced in the presence of a MPSF preferably belong to the TGF-β protein superfamily. Members of the TGF-β superfamily are divided further into families based on their degree of structural or functional similarity. The BMP family is one such family, named for its representative bone morphogenetic/osteogenic protein family members. Of the reported "BMPs" (BMP-1 to BMP-13), isolated primarily based on sequence homology, all but BMP-1 remain classified as members of the BMP family of morphogenic proteins (Ozkaynak et al., *EMBO J.*, 9, pp. 2085–93 (1990)).

The BMP family includes other structurally-related members which are morphogenic proteins, including the drosophila decapentaplegic gene complex (DPP) products, the Vg1 product of *Xenopus laevis* and its murine homolog, Vgr-1 (see, e.g., Massagué, J., "The Transforming Growth Factor-β Family", *Annu. Rev. Cell Biol.*, 6, pp. 597–641 (1990)).

A morphogenic protein according to this invention belongs to the BMP family when it comprises a polypeptide having at least 50% amino acid sequence identity with at least one known BMP family member, within the conserved C-terminal cysteine-rich domain which characterizes the BMP protein family. This definition is in part derived from comparing amino acid sequence identities between C-terminal domains of other BMP family members that have demonstrable morphogenic activity.

The Drosophila DPP and Xenopus Vg-1 gene products are 50% identical to each other (and 35–40% identical to TGF-β). Both the Dpp and Vg-1 products are morphogenic proteins that participate in early patterning events during embryogenesis of their respective hosts. These products appear to be most closely related to mammalian bone morphogenetic proteins BMP-2 and BMP-4, whose C-terminal domains are 75% identical with that of Dpp.

The C-terminal domains of BMP-3, BMP-5, BMP-6, and OP-1 (BMP-7) are about 60% identical to that of BMP-2, and the C-terminal domains of BMP-6 and OP-1 are 87% identical. BMP-6 is likely the human homolog of the murine Vgr-1 (Lyons et al., *Proc. Natl. Acad. Sci. U.S.A.*, 86, pp. 4554–59 (1989)); the two proteins are 92% identical overall at the amino acid sequence level (U.S. Pat. No. 5,459,047, incorporated herein by reference). BMP-6 is 58% identical to the Xenopus Vg-1 product.

The DNA and amino acid sequences of these and other BMP family members are published and may be used by those of skill in the art to determine whether a new candidate gene product belongs to the BMP family. New BMP-related gene products are expected by analogy to possess at least one morphogenic activity.

Another characteristic of the BMP protein family members is their apparent ability to dimerize. Several bone-derived osteogenic proteins (OPs) and BMPs are found as homo- and heterodimers in their active forms. The ability of OPs and BMPs to form heterodimers may confer additional or altered morphogenic inductive capabilities on morphogenic proteins. Heterodimers may exhibit qualitatively or quantitatively different binding affinities than homodimers for OP and BMP receptor molecules. Altered binding affinities may in turn lead to differential activation of receptors that mediate different signalling pathways, which may ultimately lead to different biological activities or outcomes.

Altered binding affinities could also be manifested in a tissue or cell type-specific manner, thereby inducing only particular progenitor cell types to undergo proliferation and/or differentiation.

Suitable in vitro, ex vivo and in vivo bioassays known in the art, including those described herein, may be used to ascertain whether a new BMP-related gene product or a new heteromeric species has a known or a new morphogenic activity. Expression and localization studies defining where and when the gene and its product(s) are expressed may also be used to identify potential morphogenic activities. Nucleic acid and protein localization procedures are well known to those of skill in the art (see, e.g., Ausubel et al., eds. *Current Protocols in Molecular Cloning*, Greene Publishing and Wiley Interscience, New York, 1989).

Many of the identified BMPs are osteogenic and can induce bone and cartilage formation when implanted into mammals. Some BMPs identified based on sequence homology to osteogenic proteins possess other morphogenic activities and the MPSFs according to this invention may be used to enhance those other activities. For example, BMP-12 and BMP-13 reportedly induce ectopic formation of tendon/ligament-like tissue when implanted into mammals (Celeste et al., WO 95/16035). Using this bioassay, or any other suitable assay selected by the skilled practitioner, one or more MPSFs that are capable of stimulating the ability of the BMP to induce tendon/ligament-like tissue formation can be identified and optimized according to the procedures described herein.

Certain BMPs which are known to be osteogenic can also induce neuronal cell differentiation. Embryonic mouse cells treated with BMP-2 or OP-1 (BMP-7) differentiate into astrocyte-like (glial) cells, and peripheral nerve regeneration using BMP-2 has been recently reported (Wang et al., WO 95/05846). In addition, BMP-4, BMP-5 and OP-1 (BMP-7) are expressed in epidermal ectoderm flanking the neural plate. Ectopic recombinant BMP-4 and OP-1 (BMP-7) proteins are capable of inducing neural plate cells to initiate dorsal neural cell fate differentiation (Liem et al., *Cell*, 82, pp. 969–79 (1995)). At the spinal cord level, OP-1 and other BMPs can induce neural crest cell differentiation. It is suggested that OP-1 and these BMPs can induce many or all dorsal neural cell types, including roof plate cells, neural crest cells, and commissural neurons, depending on localized positional cues.

That several osteogenic proteins originally derived from bone matrix appear to be localized to embryonic nervous system and to have neurogenic inductive properties makes it likely that these and other members of the BMP protein family will have additional tissue inductive properties that are not yet disclosed. It is envisioned that the ability to enhance tissue inductive properties of morphogenic proteins using a MPSF as set forth herein will be useful for enhancing new tissue inductive properties of known morphogenic proteins. It is also envisioned that the invention described herein will be useful for stimulating tissue inductive activities of new morphogenic proteins that belong to the BMP protein family as they are identified in the future.

Production of Morphogenic Proteins

The morphogenic proteins whose activity is enhanced in the presence of a MPSF according to this invention may be derived from a variety of sources. Morphogenic proteins may be isolated from natural sources, or may be produced by expressing an appropriate recombinant DNA molecule in a host cell. In addition, the morphogenic proteins of this invention may be derived synthetically and synthetic morphogenic proteins may optionally be expressed from a recombinant DNA molecule in a host cell.

1. Naturally-derived morphogenic proteins

In one embodiment of this invention, morphogenic proteins are isolated from natural sources and used in concert with a MPSF to induce tissue formation. Morphogenic proteins may be purified from tissue sources, preferably mammalian tissue sources, using conventional physical and chemical separation techniques well known to those of skill in the art. If a purification protocol is unpublished, as for a newly-identified morphogenic protein for example, conventional protein purification techniques may be performed in combination with morphogenic activity assays following each step to trace the morphogenic activity through a series of purification steps thereby establishing a viable purification scheme. When available, immunological reagents may be used alone or in conjunction with the above techniques to purify morphogenic proteins.

This invention also provides native forms of osteogenic protein that act in concert with a MPSF to induce tissue formation. Osteogenic protein may be purified from natural sources according to protocols set forth, for example, in Oppermann et al., U.S. Pat. Nos. 5,324,819 and 5,354,557, which are hereby incorporated by reference (see Example 1).

The osteogenic protein OP-1 has been described (see, e.g., Oppermann et al., U.S. Pat. No. 5,354,557). In its native form, OP-1 is glycosylated and has an apparent molecular weight of about 30–35 kD as determined by SDS-PAGE. When reduced, the 30–35 kD protein gives rise to two glycosylated polypeptide chains having apparent molecular weights that may range from about 15 kD to about 23 kD. In the reduced state, the 30–35 kD protein has no detectable osteogenic activity. The deglycosylated protein, which has osteogenic activity, has an apparent molecular weight of about 27 kD. When reduced, the 27 kD protein gives rise to the two deglycosylated polypeptides having molecular weights of about 14 kD to 16 kD.

The natural osteogenic proteins of this invention that act in concert with a MPSF to induce tissue formation may include forms having varying glycosylation patterns, varying N-termini, and active truncated or mutated forms of native protein.

2. Recombinantly-expressed Morphogenic Proteins

In another embodiment of this invention, a morphogenic protein is produced by the expression of an appropriate recombinant DNA molecule in a host cell and is used in concert with a MPSF to induce tissue formation. The DNA and amino acid sequences of many BMPs and OPs have been reported, and methods for their recombinant production are published and otherwise known to those of skill in the art. For a general discussion of cloning and recombinant DNA technology, see Ausubel et al., supra; see also Watson et al., *Recombinant DNA*, 2d ed. 1992 (W. H. Freeman and Co., New York).

The DNA sequences encoding bovine and human BMP-2 (formerly BMP-2A) and BMP-4 (formerly BMP-2B), and processes for recombinantly producing the corresponding proteins are described in U.S. Pat. Nos. 5,011,691; 5,013,649; 5,166,058 and 5,168,050.

The DNA and amino acid sequences of human and bovine BMP-5 and BMP-6, and methods for their recombinant production, are disclosed in U.S. Pat. No. 5,106,748, and U.S. Pat. No. 5,187,076, respectively; see also U.S. Pat. Nos. 5,011,691 and 5,344,654. Oppermann et al., U.S. Pat. Nos. 5,011,691 and 5,258,494, disclose DNA and amino acid sequences encoding OP-1 (BMP-7), and methods for OP-1 recombinant expression. For an alignment of BMP-2, BMP-4, BMP-5, BMP-6 and OP-1 (BMP-7) amino acid sequences, see WO 95/16034.

DNA sequences encoding BMP-8 are disclosed in WO 91/18098, and DNA sequences encoding BMP-9 in WO 93/00432. DNA and deduced amino acid sequences encoding BMP-10 and BMP-11 are disclosed in WO 94/26893, and WO 94/26892, respectively. DNA and deduced amino acid sequences for BMP-12 and BMP-13 are disclosed in WO 95/16035.

The above patent disclosures, which describe DNA and amino acid sequences, and methods for producing the BMPs and OPs encoded by those sequences, are incorporated herein by reference.

To clone genes which encode new BMPs, OPs and other morphogenic proteins identified in extracts by bioassay, methods entailing "reverse genetics" may be employed. Such methods start with a protein of known or unknown function to obtain the gene which encodes that protein. Standard protein purification techniques may be used as an initial step in cloning the gene by reverse genetics. If enough protein can be purified to obtain a partial amino acid sequence, a degenerate DNA probe capable of hybridizing to the DNA sequence that encodes that partial amino acid sequence may be designed, synthesized and used as a probe to isolate full-length clones that encode that or a related morphogenic protein.

Alternatively, a partially-purified extract containing the morphogenic agent may be used to raise antibodies directed against that agent using immunological procedures well known in the art. Morphogenic protein-specific antibodies may then be used as a probe to screen expression libraries made from cDNAs (see, e.g., Broome and Gilbert, *Proc. Natl. Acad. Sci. U.S.A.*, 75, pp. 2746–49 (1978; Young and Davis, *Proc. Natl. Acad. Sci. U.S.A.*, 80, pp. 31–35 (1983)).

For cloning and expressing new BMPs, OPs and other morphogenic proteins identified based on DNA sequence homology, the homologous sequences may be cloned and sequenced using standard recombinant DNA techniques. With the DNA sequence available, a DNA fragment encoding the morphogenic protein may be inserted into an expression vector selected to work in conjunction with a desired host expression system. The DNA fragment is cloned into the vector such that its transcription is controlled by a heterologous promoter in the vector, preferably a promoter which may be optionally regulated.

Some host-vector systems that are appropriate for the recombinant expression of BMPs and OPs are disclosed in the references cited above. Useful host cells include but are not limited to bacteria such as *E. coli*, yeasts such as Saccharomyces and Picia, insect-baculovirus cell system, and primary, transformed or immortalized eukaryotic cells in culture. Preferred eukaryotic host cells include CHO, COS and BSC cells (see below).

An appropriate vector is selected according to the host system selected. Useful vectors include but are not limited to plasmids, cosmids, bacteriophage, insect and animal viral vectors, including retroviruses, and other single and double-stranded DNA viruses.

In one embodiment of this invention, the morphogenic protein used in concert with a MPSF may be derived from a recombinant DNA molecule expressed in a prokaryotic host (Example 2A). Using recombinant DNA techniques, various fusion genes have been constructed to induce recombinant expression of naturally-sourced osteogenic sequences in *E. coli* (see, e.g., Oppermann et al., U.S. Pat. No. 5,354,557, incorporated herein by reference). Using analogous procedures, DNAs comprising truncated forms of naturally-sourced morphogenic sequences may be prepared as fusion constructs linked by the acid labile cleavage site (Asp-Pro) to a leader sequence (such as the "MLE leader") suitable for promoting expression in *E. coli*.

In another embodiment of this invention, the morphogenic protein used in concert with a MPSF is expressed using a mammalian host/vector system (Example 2B). It may be preferable to recombinantly produce a mammalian protein for therapeutic uses in mammalian cell culture systems in order to produce a protein whose structure resembles more closely that of the natural material. Recombinant protein production in mammalian cells requires the establishment of appropriate cells and cell lines that are easy to transfect, are capable of stably maintaining foreign DNA with an unrearranged sequence, and which have the necessary cellular components for efficient transcription, translation, post-translational modification and secretion of the protein. In addition, a suitable vector carrying the gene of interest is necessary.

DNA vector design for transfection into mammalian cells should include appropriate sequences to promote expression of the gene of interest, including: appropriate transcription initiation, termination and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion.

Preferred DNA vectors also include a marker gene and means for amplifying the copy number of the gene of interest. DNA vectors may also comprise stabilizing sequences (e.g., ori- or ARS-like sequences and telomere-like sequences), or may alternatively be designed to favor directed or non-directed integration into the host cell genome.

Substantial progress in the development of mammalian cell expression systems has been made in the last decade and many aspects of the system are well characterized. A detailed review of the production of foreign proteins in mammalian cells, including useful cells, protein expression-promoting sequences, marker genes, and gene amplification methods, is disclosed in M. M. Bendig, *Genetic Engineering*, 7, pp. 91–127 (1988).

Particular details of the transfection, expression and purification of recombinant proteins are well documented and are understood by those of skill in the art. Further details on the various technical aspects of each of the steps used in recombinant production of foreign genes in mammalian cell expression systems can be found in a number of texts and laboratory manuals in the art. See, e.g., F. M. Ausubel et al., ed., *Current Protocols in Molecular Biology*, John Wiley & Sons, New York (1989).

Briefly, among the best characterized transcription promoters useful for expressing a foreign gene in a particular mammalian cell are the SV40 early promoter, the adenovirus major late promoter (AdMLP), the mouse metallothionein-I promoter (mMT-I), the Rous sarcoma virus (RSV) long terminal repeat (LTR), the mouse mammary tumor virus long terminal repeat (MMTV-LTR), and the human cytomegalovirus major intermediate-early promoter (hCMV). The DNA sequences for all of these promoters are known in the art and are available commercially.

One method of gene amplification in mammalian cell systems is the use of the selectable dihydrofolate reductase (DHFR) gene in a dhfr- cell line. Generally, the DHFR gene is provided on the vector carrying the gene of interest, and addition of increasing concentrations of the cytotoxic drug methotrexate (MTX) leads to amplification of the DHFR gene copy number, as well as that of the physically-associated gene of interest. DHFR as a selectable, amplifiable marker gene in transfected chinese hamster ovary cell lines (CHO cells) is particularly well characterized in the art. Other useful amplifiable marker genes include the adenosine deaminase (ADA) and glutamine synthetase (GS) genes.

In a preferred expression system, gene amplification is further enhanced by modifying marker gene expression regulatory sequences (e.g., enhancer, promoter, and transcription or translation initiation sequences) to reduce the levels of marker protein produced. Lowering the level of DHFR transcription increases the DHFR gene copy number (and the physically-associated gene) to enable the transfected cell to adapt to growth in even low levels of methotrexate (e.g., 0.1 µM MTX). Preferred expression vectors such as pH754 and pH752 (Oppermann et al., U.S. Pat. No. 5,354,557, FIGS. 19C and D), have been manipulated using standard recombinant DNA technology, to create a weak DHFR promoter. As will be appreciated by those skilled in the art, other useful weak promoters, different from those disclosed and preferred herein, can be constructed using standard vector construction methodologies. In addition, other, different regulatory sequences also can be modified to achieve the same effect.

Another gene amplification scheme relies on the temperature sensitivity (ts) of BSC40-tsA58 cells transfected with an SV40 vector. Temperature reduction to 33° C. stabilizes the temperature sensitive SV40 T antigen, which leads to the excision and amplification of the integrated transfected vector DNA thereby amplifying the physically associated gene of interest.

The choice of cells/cell lines is also important and depends on the needs of the skilled practitioner. Monkey kidney cells (COS) provide high levels of transient gene expression providing a useful means for rapidly testing vector construction and the expression of cloned genes. COS cells are transfected with a simian virus 40 (SV40) vector carrying the gene of interest. The transfected COS cells eventually die, thus preventing the long term production of the desired protein product. However, transient expression does not require the time consuming process required for the development of stable cell lines.

CHO cells are capable of successfully expressing a wide variety of proteins from a broad range of cell types. Thus, while the glycosylation pattern on a recombinant protein produced in a mammalian cell expression system may not be identical to the natural protein, the differences in oligosaccharide side chains are often not essential for biological activity of the expressed protein.

Several different mammalian cell expression systems may be used to express recombinant morphogenic proteins to use in concert with a MPSF according to this invention. Stable cell lines have been developed using CHO cells and a temperature-sensitive (ts) strain of BSC cells (simian kidney cells, BSC40-tsA58; Biotechnology, 6, pp. 1192–96 (1988)) for the long term production of osteogenic protein OP-1. Among established cell lines, CHO cells may be the best characterized to date, and are a preferred cell line for mammalian cell expression of recombinant morphogenic proteins (Example 2b).

Two different promoters were found most useful to transcribe human osteogenic protein sequences (hOP1; SEQ. ID No. 1): the CMV promoter and the MMTV promoter, boosted by the enhancer sequence from the Rous sarcoma virus LTR. The mMT promoter (mouse metallothionein promoter) and the SV40 late promoter have also been tested. Several selection marker genes such as neo (neomycin) and DHFR are used.

Restriction maps and sources of various exemplary expression vectors designed for OP-1 expression in mammalian cells have been described in Oppermann et al., U.S. Pat. No. 5,354,557, incorporated herein by reference (see Example 2B). Each of these vector constructs employs a full-length human OP-1 cDNA sequence cloned into a conventional pUC vector (pUC-18).

It will be appreciated by those of skill in the art that DNA sequences encoding truncated forms of osteogenic protein may also be used, provided that the expression vector or host cell then provides the sequences necessary to direct processing and secretion of the expressed protein.

Recombinant OP-1 has been expressed in three different cell expression systems: COS cells for rapidly screening the functionality of the various expression vector constructs, CHO cells for the establishment of stable cell lines, and BSC40-tsA58 cells as an alternative means of producing recombinant OP-1 protein. The CHO cell expression system disclosed herein is contemplated to be the best mode currently known for long-term recombinant OP-1 production in mammalian cells (see Example 2B).

As discussed above, several bone-derived osteogenic proteins (OPs) and BMPs are found as homo- and heterodimers comprising interchain disulfide bonds in their active forms. Methods for co-expressing and assembling heteromeric polypeptide subunits in a host have been described (see, e.g., WO 93/09229, which is incorporated herein by reference). BMP-2, BMP-4, BMP-6 and BMP-7 (OP-1)—originally isolated from bone—are bioactive as either homodimers or heterodimers.

In addition, methods for making amino acid substitution mutations in BMPs and OPs that favor refolding and/or assembling subunits into forms that exhibit greater morphogenic activity have also been described (U.S. Pat. No. 5,399,677, which is incorporated herein by reference).

Synthetic Non-native Morphogenic Proteins

In another embodiment of this invention, a morphogenic protein may be prepared synthetically for use in concert with a MPSF to induce tissue formation. Morphogenic proteins prepared synthetically may be native, or may be non-native proteins, i.e., those not otherwise found in nature.

Non-native osteogenic proteins have been synthesized using a series of consensus DNA sequences (U.S. Pat. No. 5,324,819, incorporated herein by reference). These consensus sequences were designed based on partial amino acid sequence data obtained from natural osteogenic products and on their observed homologies with other genes reported in the literature having a presumed or demonstrated developmental function.

Several of the biosynthetic consensus sequences (called consensus osteogenic proteins or "COPs") have been expressed as fusion proteins in prokaryotes. Purified fusion proteins may be cleaved, refolded, combined with at least one MPSF (optionally in a matrix or device), implanted in an established animal model and shown to have bone- and/or cartilage-inducing activity. The currently preferred synthetic osteogenic proteins comprise two synthetic amino acid sequences designated COP5 (Seq. ID No. 2) and COP7 (Seq. ID No. 3).

The amino acid sequences of these proteins are shown below, as set forth in Oppermann et al., U.S. Pat. Nos. 5,011,691 and 5,324,819, which are incorporated herein by reference:

```
COP5      LYVDFS-DVGWDDWIVAPPGYQAFYCHGECPFPLAD
COP7      LYVDFS-DVGWNDWIVAPPGYHAFYCHGECPFPLAD

COP5      HFNSTN--H-AVVQTLVNSVNKI--PKACCVPTELSA
COP7      HLNSTN--H-AVVQTLVNSVNKI--PKACCVPTELSA

COP5      ISMLYLDENEKVVLKYNQEMVVEGCGCR
COP7      ISMLYLDENEKVVLKYNQEMVVEGCGCR
```

In these amino acid sequences, the dashes (-) are used as fillers only to line up comparable sequences in related proteins. Differences between the aligned amino acid sequences are highlighted.

Thus in one embodiment of this invention, the morphogenic protein which acts in concert with a MPSF to induce tissue formation is a synthetic osteogenic protein comprising a partial or the complete amino acid sequence of COP5 or COP7 such that it is capable of inducing tissue formation such as cartilage and/or bone formation in the presence of a MPSF when properly folded and implanted in a mammal.

COP proteins may be used in the presence of a MPSF to induce bone formation from osteoblasts when implanted in a favorable environment. Alternatively, COP proteins may be used in concert with a MPSF to produce cartilage if implanted in an avascular locus or if an inhibitor to full bone development is implanted together with or present in the vicinity of the active morphogenic protein.

Preferably, the synthetic morphogenic protein which acts in concert with a MPSF of this invention comprises a protein which comprises a sequence sufficiently duplicative of the sequence of COP5 or COP7 such that it is capable of tissue formation such as bone and/or cartilage formation when properly folded and implanted in a mammal in the presence of a MPSF. More preferably, the protein is less than about 200 amino acids long.

In one preferred embodiment, these synthetic proteins comprise species of the generic amino acid sequences:

```
1         10        20        30        40        50
CXXXXLXVXFXDXGWXXWXXXPXGXXAXYCXGXCXXPXXXXXXXXXNHAXX 60        70        80        90       100
QXXVXXXNXXXXPXXCCXPXXXXXXXXLXXXXXXXXVXLXXYXXMXVXXCXCX ;
``` or

```
1         10        20        30        40        50
    LXVXFXDXGWXXWXXXPXGXXAXYCXGXCXXPXXXXXXXXXNHAXX 60        70        80        90       100
QXXVXXXNXXXXPXXCCXPXXXXXXXXLXXXXXXXXVXLXXYXXMXVXXCXCX
``` where the letters indicate the amino acid residues of standard single letter code, and the Xs represent amino acid residues (residues 1–102 and 5–102 of Seq. ID No. 4). Cysteine residues are highlighted.

Preferred amino acid sequences within the foregoing generic sequences are:

```
1         10        20        30        40        50
    LYVDFRDVGWNDWIVAPPGYHAFYCHGECPFPLADHLNSTNHAIV
    K S S L  QE VIS E FD Y  E A AY MPESMKAS      VI
    F E K I  DN     L    N  S   Q ITK F P        TL
        A     S        K 60        70        80        90       100
QTLVNSVNPGKIPKACCVPTELSAISMLYLDENENVVLKNYQDMVVEGCGCR
 SI HAI SEQV EP    EQMNSLAI FFNDQDK I RK EE  T DA H H
    RF    T  S     K DPV V  Y N S      H RN    RS
    N     S                 K            P     E
``` and

```
1         10        20        30        40        50
CKRHPLYVDFRDVGWNDWIVAPPGYHAFYCHGECPFPLADHLNSTNHAIV
RRRS K S S L  QE VIS E FD Y  E A AY MPESMKAS      VI
   KE F E K I DN     L    N  S   Q ITK F P        TL
Q         A    S        K 60        70        80        90       100
QTLVNSVNPGKIPKACCVPTELSAISMLYLDENENVVLKNYQDMVVEGCGCR
 SI HAI SEQV EP    EQMNSLAI FFNDQDK I RK RR  T DA H H
    RF    T  S     K DPV V  Y N S      H RN    RS
    N     S                 K            P     E
``` wherein each of the amino acids arranged vertically at each position in the sequence may be used alternatively in various combinations (Seq. ID No. 5). Note that these generic sequences have 6 and preferably 7 cysteine residues where inter- or intramolecular disulfide bonds can form, and contain other critical amino acids which influence the tertiary structure of these osteogenic proteins.

Synthetic non-native osteogenic proteins may be chemically synthesized or may be recombinantly expressed by introducing the synthetic DNA sequences on an expression vector into a host cell using procedures described above for recombinant expression of native protein sequences. These biosynthetic COP sequences are believed to dimerize during refolding, and appear not to be active when reduced. Homodimers or heterodimers may be assembled.

These and other synthetic non-native osteogenic proteins may be used in concert with a MPSF and tested using in vitro, ex vivo or in vivo bioassays for progenitor cell induction and tissue regeneration according to the procedures described herein. It is envisioned that non-native osteogenic protein/MPSF combinations will be capable of inducing differentiation of certain neural lineages that can be induced by native osteogenic proteins.

It is also envisioned that non-native osteogenic proteins in concert with a MPSF will be capable of inducing other types of progenitor cells to differentiate and proliferate. Thus non-native osteogenic protein and MPSF may be useful for the repair and regeneration not only of bone and cartilage tissue, but also of tendon, ligament, neural and potentially other types of tissue, and will thus be useful generally for tissue repair and regeneration procedures.

Homologous Proteins Having Morphogenic Activity

The morphogenic proteins which act in concert with a MPSF to induce tissue formation according to this invention may be produced by the recombinant expression of DNA sequences isolated based on homology with the osteogenic COP consensus sequences described above. Synthetic COP sequences such as those described above may be used as probes to retrieve related DNA sequences from a variety of species (see, e.g., Oppermann et al., U.S. Pat. Nos. 5,011, 591 and 5,258,494, which are incorporated herein by reference). COP sequences have retrieved genomic DNAs which were subsequently shown, when properly assembled, to encode proteins which have true osteogenic activity, i.e., induce the full cascade of events when properly implanted in a mammal leading to bone formation. Genomic DNAs encoding BMP-2 and OP-1 (BMP-7), for example, were isolated using this procedure.

Morphogenic proteins that are encoded by a gene which hybridizes with a COP sequence probe are preferably assembled into a pair of subunits disulfide bonded to produce a dimeric species capable of inducing tissue formation when implanted in the presence of a MPSF into a mammal. The dimeric species may comprise homo- or heterodimers of the COP-related polypeptide assembled with a heterologous polypeptide. Recombinant forms of BMP-2 and BMP-4 have been shown to have cross-species osteogenic activity as homodimers and as heterodimers assembled with OP-1 (BMP-7) subunits.

Morphogenic protein-encoding genes that hybridize to synthetic COP sequence probes include genes encoding Vg1, inhibin, DPP, OP-1(BMP-7), BMP-2 and BMP-4. Vg1 is a known *Xenopus laevis* morphogenic protein involved in early embryonic patterning. Inhibin is another developmental gene that is a member of the BMP family of proteins from *Xenopus laevis*. DPP is an amino acid sequence encoded by a drosophila gene responsible for development of the dorsoventral pattern. OP-1 (also called BMP-7), BMP-2 and BMP-4 are osteogenic proteins which can induce cartilage, bone and neural tissue formation (see below). Various combinations of these polypeptides, i.e., heterodimers and homodimers, have morphogenic activity.

In another embodiment of this invention, a morphogenic protein that acts in concert with a MPSF may comprise a polypeptide encoded by a nucleic acid that can hybridize under stringent conditions to an "OPS" nucleic acid probe (Oppermann et al., U.S. Pat. No. 5,354,557). "OPS"—standing for OP-1 "short"—refers to the portion of the human OP-1 protein defining the conserved 6 cysteine skeleton in the C-terminal active region (97 amino acids; Seq. ID No. 1, residues 335–431).

One example of a stringent hybridization condition is hybridization in 4×SSC at 65° C. (or 10° C. higher than the calculated melting temperature for a hybrid between the probe and a nucleic acid sequence containing no mismatched base pairs), followed by washing in 0.1×SSC at the hybridization temperature. Another stringent hybridization condition is hybridization in 50% formamide, 4×SSC at 42° C. (see e.g., T. Maniatis et al., *Molecular Cloning (A Laboratory Manual)*, Cold Spring Harbor Laboratory, pp.387–89 (1982)).

Thus, in view of this disclosure, the skilled practitioner may design and synthesize genes, or isolate genes from cDNA or genomic libraries which encode amino acid sequences associated with morphogenic activity. These genes can be expressed in prokaryotic or eukaryotic host cells to produce large quantities of active osteogenic or otherwise morphogenic proteins. Recombinantly expressed proteins may be in native forms, truncated analogs, muteins, fusion proteins, and other constructed forms capable of inducing bone, cartilage, or other types of tissue formation as demonstrated by in vitro and ex vivo bioassays and in vivo implantation in mammals, including humans.

Once the skilled practitioner has a bioassay that can detect one or more morphogenic protein activities, a morphogenic protein stimulatory factor (MPSF) capable of stimulating that activity may be identified using the techniques described herein.

Preferred Morphogenic Proteins

In one preferred embodiment of this invention, the morphogenic protein whose activity may be stimulated by the presence of a MPSF comprises a pair of subunits disulfide bonded to produce a dimeric species, wherein at least one of the subunits comprises a recombinant polypeptide belonging to the BMP protein family. The dimeric species may be a homodimer or heterodimer and is capable of inducing cell proliferation and/or tissue formation when accessible to a progenitor cell in the mammal. The progenitor cell may be induced to form one or more tissue types pereferably selected from the group consisting of endochondral or intramembranous bone, cartilage, tendon/ligament-like tissue, neural tissue and other organ tissue types, including kidney tissue.

In another preferred embodiment, the morphogenic protein is an osteogenic protein that is capable of inducing the progenitor cell to form one or more tissue types selected from the group consisting of endochondral or intramembranous bone and cartilage.

Preferred morphogenic and osteogenic proteins of this invention comprise at least one polypeptide selected from the group consisting of BMP-2, BMP-4, BMP-5, BMP-6, OP-1 (BMP-7), BMP-8, BMP-9, BMP-10, BMP-11, BMP-12, BMP-13, COP-5 and COP-7. Preferably, the morphogenic protein comprises at least one polypeptide selected from the group consisting of OP-1 (BMP-7), BMP-2, BMP-4 and BMP-6; more preferably, OP-1 (BMP-7)and BMP-2; and most preferably, OP-1 (BMP-7).

As the skilled practitioner will appreciate, the preferred morphogenic proteins of this invention whose activity is enhanced in the presence of a MPSF will depend in part on the tissue type to be generated and on the selected implantation or treatment site. These variables may be tested empirically.

Morphogenic Protein Stimulatory Factors (MPSF)

A morphogenic protein stimulatory factor (MPSF) according to this invention is a factor that is capable of stimulating the ability of a morphogenic protein to induce tissue formation from a progenitor cell. In one embodiment of this invention, a method for improving the tissue inductive activity of a morphogenic protein in a mammal by coadministering an effective amount of a MPSF is provided. The MPSF may have an additive effect on tissue induction by the morphogenic protein. Preferably, the MPSF has a synergistic effect on tissue induction by the morphogenic protein.

The progenitor cell that is induced to proliferate and/or differentiate by the morphogenic protein of this invention is preferably a mammalian cell. Preferred progenitor cells include mammalian chondroblasts, osteoblasts and neuroblasts, all earlier developmental precursors thereof, and all cells that develop therefrom (e.g., chondroblasts, pre-chondroblasts and chondrocytes). However, morphogenic proteins are highly conserved throughout evolution, and non-mammalian progenitor cells are also likely to be stimulated by same- or cross-species morphogenic proteins and MPSF combinations. It is thus envisioned that when schemes become available for implanting xenogeneic cells into humans without causing adverse immunological reactions, non-mammalian progenitor cells stimulated by morphogenic protein and a MPSF according to the procedures set forth herein will be useful for tissue regeneration and repair in humans.

One or more MPSFs are selected for use in concert with one or more morphogenic proteins according to the desired tissue type to be induced and the site at which the morphogenic protein and MPSF will be administered. The particular choice of a morphogenic protein(s)/MPSF(s) combination and the relative concentrations at which they are combined may be varied systematically to optimize the tissue type induced at a selected treatment site using the procedures described herein.

The preferred morphogenic protein stimulatory factors (MPSFs) of this invention are selected from the group consisting of hormones, cytokines and growth factors. Most preferred MPSFs for inducing bone and/or cartilage formation in concert with an osteogenic protein comprise at least one compound selected from the group consisting of insulin-like growth factor I (IGF-I), estradiol, fibroblast growth factor (FGF), growth hormone (GH), growth and differentiation factor (GDF), hydrocortisone (HC), insulin, progesterone, parathyroid hormone (PTH), vitamin D (1,25-$(OH)_2D_3$), retinoic acid and an interleukin, particularly IL-6. When the progenitor cell is an osteoblast stimulated to form bone, preferred osteogenic protein/MPSF combinations exclude BMP-2 or BMP-3 homodimers used in concert with vitamin D or PTH.

In another preferred embodiment of this invention, the MPSF comprises a compound or an agent that is capable of increasing the bioactivity of another MPSF. Agents that increase MPSF bioactivity include, for example, those that increase the synthesis, half-life, reactivity with other biomolecules such as binding proteins and receptors, or the bioavailability of the MPSF. These agents may comprise hormones, growth factors, peptides, cytokines, carrier molecules such as proteins or lipids, or other factors that increase the expression or the stability of the MPSF.

For example, when the selected MPSF is IGF-I, agents that increase its bioactivity include GH, PTH, vitamin D, and cAMP inducers, which may thus function as MPSFs according to this invention. In addition, almost all of the IGF-I in circulation and the extracellular space is bound by a group of high affinity binding proteins called IGFBPs which can augment or inhibit IGF-I bioactivity (see, e.g., Jones and Clemmons, *Endocrine Reviews*, 16, pp. 3–34 (1995)). Thus IGFBPs and agents which alter the levels of IGFBPs such that the bioactive IGF-I concentration is ultimately increased will also function as a MPSF according to this invention.

These or other agents that increase IGF-I bioactivity may be used alone as the primary MPSF, or one or more may be used as additional MPSFs in combination with IGF-I, to stimulate the tissue inductive activity of the morphogenic protein. One such preferred combination comprising at least two MPSFs for cartilage and bone formation is osteogenic protein OP-1, IGF-I and PTH (see below).

Preferably, the MPSF is present in an amount capable of synergistically stimulating the tissue inductive activity of the morphogenic protein in a mammal. The relative concentrations of morphogenic protein and MPSF that will optimally induce tissue formation when administered to a mammal may be determined empirically by the skilled practitioner using the procedures described herein.

Testing Putative Morphogenic Protein Stimulatory Factors

To identify a MPSF that is capable of stimulating the tissue inductive activity of a chosen morphogenic protein, an appropriate assay must be selected. Initially, it is preferable to perform in vitro assays to identify a MPSF that is capable of stimulating the tissue inductive activity of a morphogenic protein. A useful in vitro assay is one which monitors a nucleic acid or protein marker whose expression is known to correlate with the associated cell differentiation pathway.

Examples 3 and 4 describe experiments using the osteogenic protein OP-1 to identify and to optimize an effective concentration of MPSF. As described above, OP-1 is known to have osteogenic and neurogenic activity. Thus an in vitro assay looking at the expression of either an osteo- or neurogenic-associated marker in appropriately corresponding progenitor cells can be used to identify one or more MPSFs that function in concert with OP-1.

A preferred assay for testing potential MPSFs with OP-1 for osteogenic activity is the alkaline phosphatase (AP) enzymatic assay. AP is an osteoblast differentiation marker in primary osteoblastic FRC (fetal rat calvarial) cells. The OP-1-stimulated AP activity is the result of increased steady-state AP mRNA levels as measured by Northern analysis. The procedure is generally as follows.

First, a MPSF is identified by picking one or more concentrations of a MPSF and testing them alone or in the presence of a morphogenic protein (Examples 3 and 4). Second, the amount of MPSF required to achieve optimal, preferably synergistic, tissue induction in concert with the morphogenic protein is determined by generating a dose response curve (Example 3).

Optionally, one or more additional MPSFs that stimulate or otherwise alter the morphogenic activity induced by a morphogenic protein and a first MPSF may be identified and a new multi-factor dose response curve generated (Example 5).

Levels for additional biochemical markers for bone cell differentiation may be measured to assay for synergistic effects of OP-1 and other proteins belonging to the BMP family with IGF-I and other IGF-I activating agents. Other bone cell differentiation markers include but are not limited to: type I collagen, osteocalcin, osteopontin, bone sialoprotein and PTH-dependent cAMP levels.

FIG. 1 shows that IGF-I can act as a MPSF which stimulates the osteogenic activity of OP-1. Exogenous IGF-I elicits a stimulatory effect on the ability of OP-1 to induce FRC cell differentiation as monitored by levels of cellular alkaline phosphatase (AP) activity. Exogenous IGF-I alone (up to 300 ng/ml) did not stimulate AP activity in FRC cells. However, IGF-I enhanced the OP-1-stimulated AP activity by 3–4 fold. Thus the stimulatory effect of IGF-I is synergistic.

Figure 2:
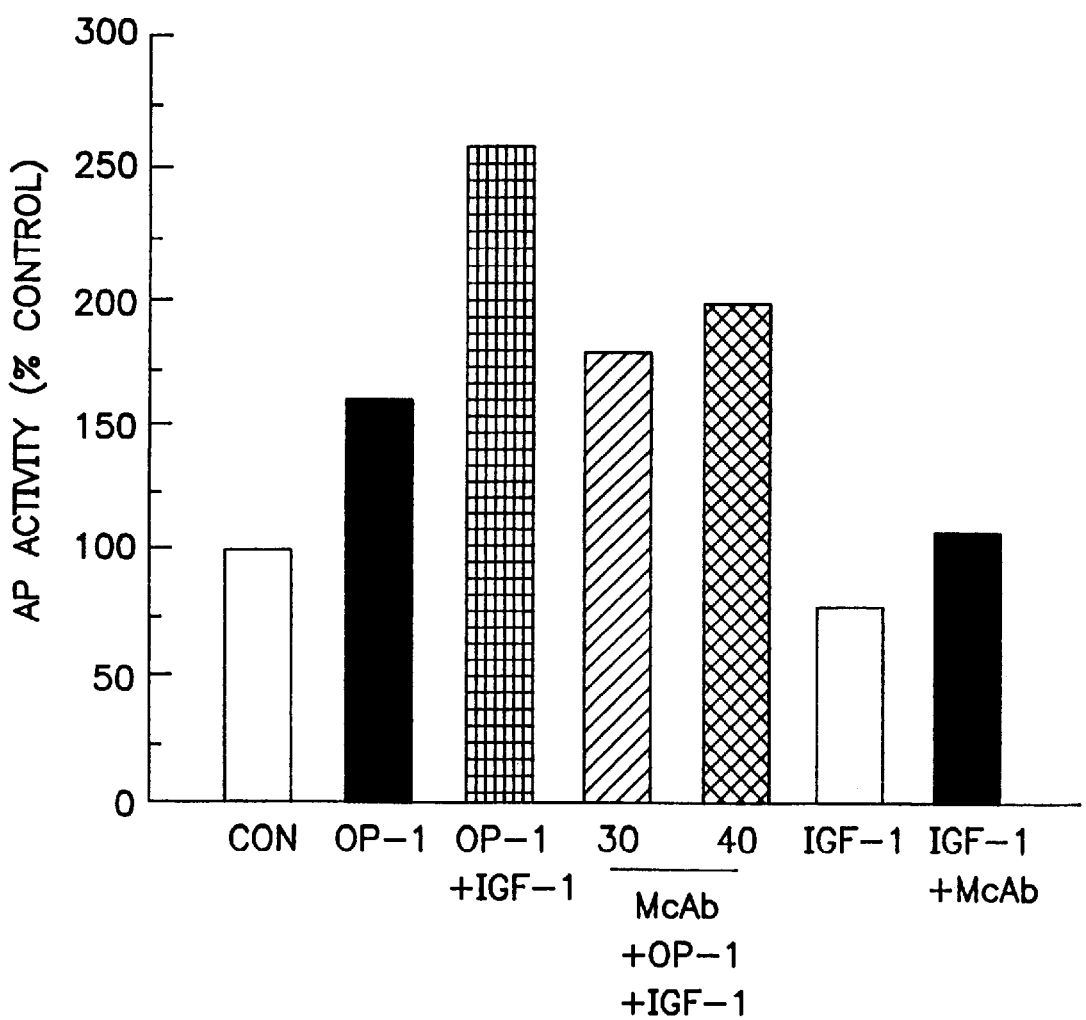
FIG. 2. Anti-IGF-I monoclonal antibodies inhibit IGF-I stimulation of OP-1 osteogenic induction. FRC cells were incubated with a monoclonal antibody (Upstate Biotech) against IGF-I for 48 hours in the presence or absence of OP-1 (500 ng/ml). The level of alkaline phosphatase (nmol/$\mu$g protein) in each culture was measured.

To show that the MPSF activity of IGF-I was not due to a contaminating factor present in the IGF-I preparation used in the above experiment, a similar experiment was performed in the presence or absence of an IGF-I-specific antibody that blocks the action of IGF-I. As shown in FIG. 2, anti-IGFI antibody blocked, at least partially, the OP-1-stimulated alkaline phosphatase activity. Whereas OP-1 (500 ng/ml) stimulated AP activity by 1.6 fold above the vehicle-treated control culture, co-incubation with anti-IGF-I antibody reduced the magnitude of the OP-1-induced stimulation about 50%. Increasing the amount of antibody did not reduce the magnitude, suggesting that the amount of antibody was not a limiting factor.

These results demonstrate that OP-1-induced differentiation of osteoblastic cells may be stimulated by increasing IGF-I levels.

Once a morphogenic protein/MPSF pair has been identified, it is desirable to identify the relative amounts of each component that are required to effectuate optimal levels of tissue inductive activity when the two components work in concert. This is done by assaying the tissue inductive activity produced when the concentration of each component is systematically varied independently from the other. The result of such a study is a dose response curve for a given morphogenic protein/MPSF pair.

Figure 3:
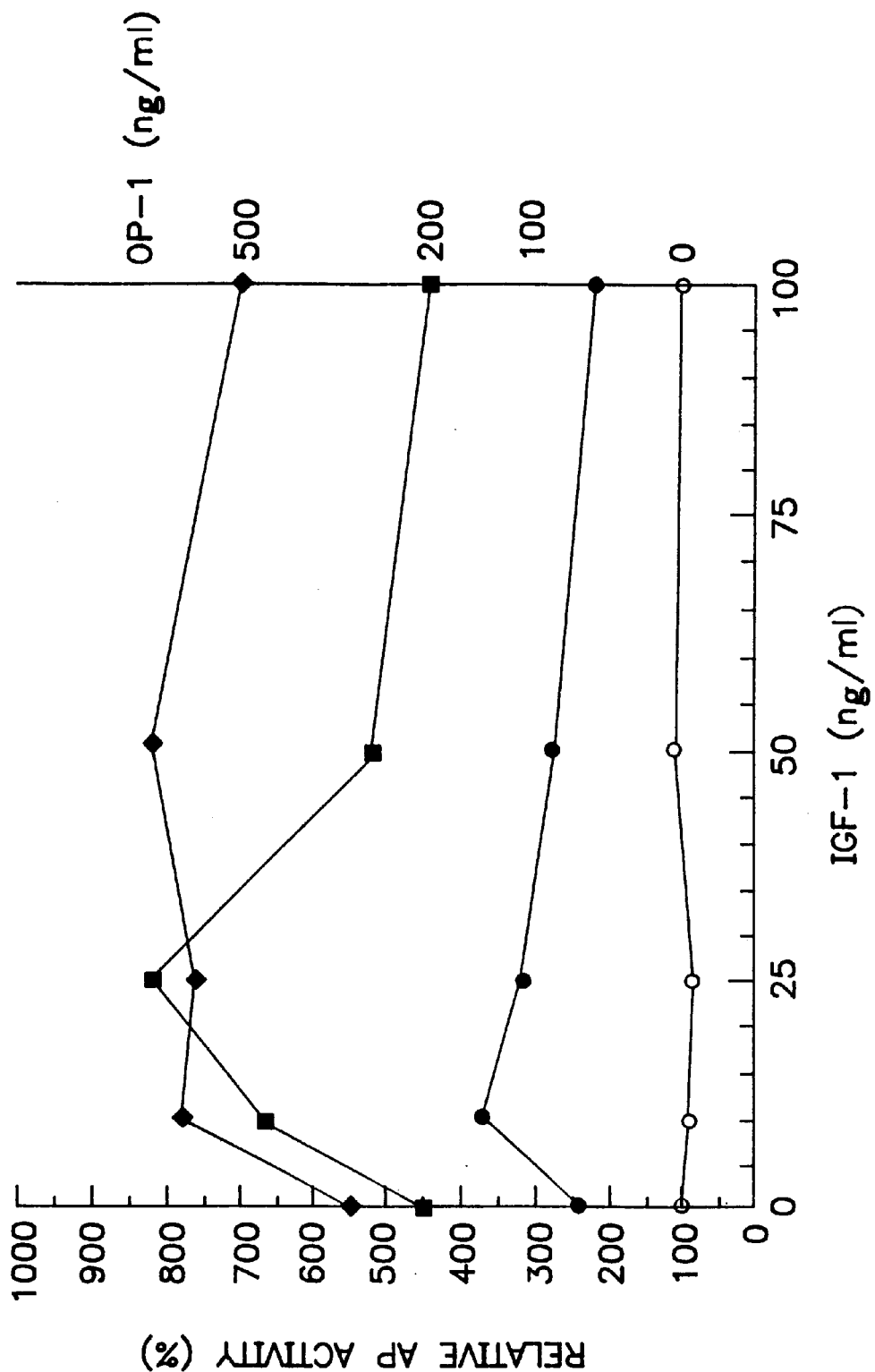
FIG. 3. IGF-I and OP-1 dose response curves for bone inductive activity. Relative alkaline phosphatase (AP) activity (%) in FRC cells is plotted as a function of increasing IGF-I concentrations (purchased from BRL; 0–100 ng/ml) in the absence or presence of increasing concentrations of OP-1 (0–500 ng/ml).

FIG. 3 shows the effect of varying IGF-I concentration (1–100 ng/ml) as a function of OP-1 concentration (0–500 ng/ml) on the synergistic enhancement of bone inducing activity. In the absence of OP-1, IGF-I did not stimulate AP activity in FRC cells. However, at a OP-1 concentration of 100 ng/ml, even a low concentration (10 ng/ml) of IGF-I potentiated the OP-1-stimulated AP activity by 1.5–2 fold. A maximum enhancement (about 2.5-fold) was observed at 25 ng/ml of IGF-I at an OP-1 concentration of 200 ng/ml. IGF-I at higher concentrations no longer potentiates the OP-1-stimulated AP activity. At these higher IGF-I concentrations, the OP-1-stimulated increase in AP activity is not inhibited.

Other factors still to be identified may also influence OP-1 inductive activity, and similar assays can be performed using OP-1 and IGF-I to identify one or more additional MPSFs that can stimulate further the osteoinductive activity of OP-1 in the presence of IGF-I (Example 5).

Figure 4:
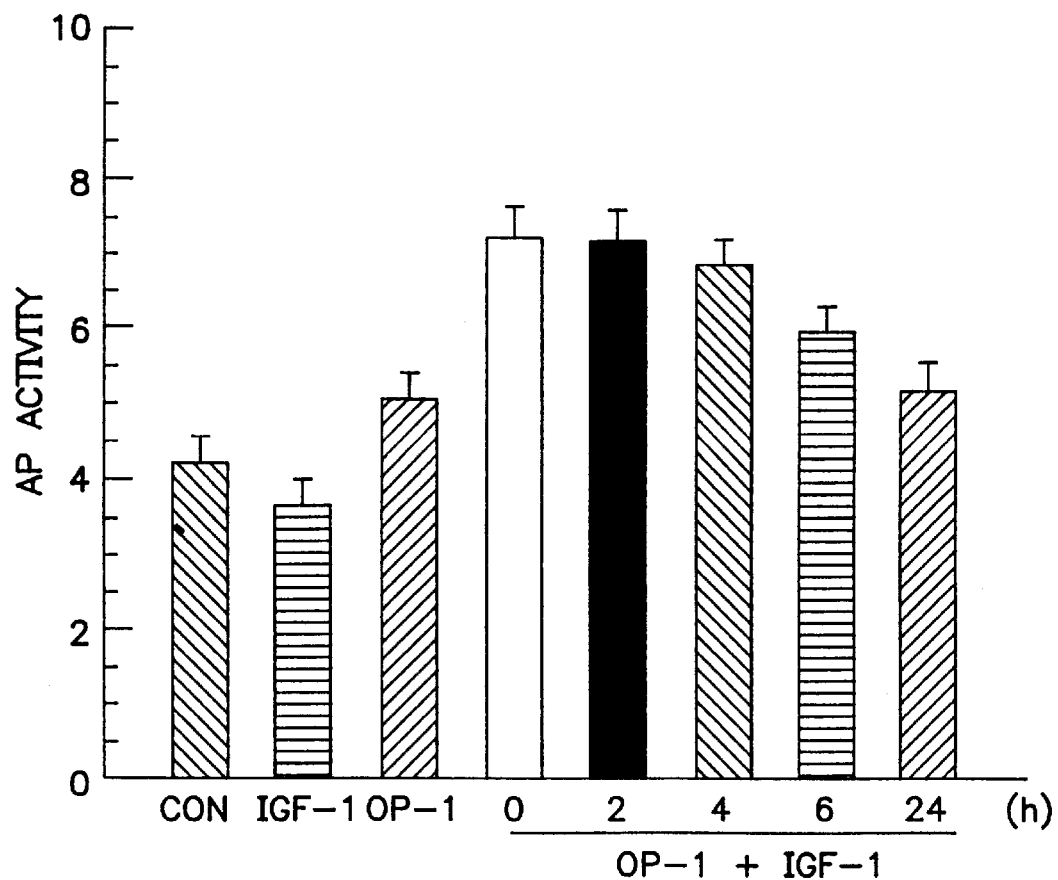
FIG. 4. Timing of OP-1 and IGF-I addition. Alkaline phosphatase (AP) activity (nmol/$\mu$g protein) in FRC cells is indicated. FRC cells were grown in serum free media containing 500 ng/ml OP-1, and IGF-I (25 ng/ml) was added to the culture at different times (hours) subsequently. Control cultures were grown in serum free media containing solvent vehicles.

To evaluate the effect of pre-treatment of FRC cells with OP-1 on the synergistic effect of IGF-I, cells were first incubated in a constant concentration of OP-1 (500 ng/ml). IGF-I (25 ng/ml) was added to the culture at different times subsequently, and the AP level was determined at the end of 48 h of incubation. FIG. 4 shows that the maximum synergistic effect was observed when FRC cells were treated with OP-1 and IGF-I simultaneously. The effect was reduced significantly if IGF-I was added 6 h or later after OP-1 treatment. Pre-incubation of FRC cells with IGF-I (25 ng/ml) for 24 h followed by OP-1 treatment (500 ng/ml) abolishes the synergistic effect. Thus when the morphogenic protein is OP-1 and the MPSF is IGF-I, it is preferred that they be administered at or at about the same time for the MPSF to have its maximum effect.

It may not hold true for every morphogenic protein/MPSF combination that co-administration is optimal for inducing morphogenic activity. For example, when the MPSF (MPSF-1) is an agent that induces the expression of another MPSF (MPSF-2), it may be found that pre-administering MPSF-1 is preferred so that high levels of MPSF-2 are present when the selected morphogenic protein is administered. The procedures described herein can be used by the skilled practitioner to optimize an administration protocol for a given morphogenic protein/MPSF combination to induce a selected tissue type at a selected treatment site.

The procedure described above for OP-1 and IGF-I may be used generally with any selected morphogenic protein to test putative MPSFs compounds (Example 4). First, the morphogenic protein or agent is used to identify and then to optimize conditions for an assay that accurately represents the induction of a particular type of cell differentiation pathway associated with tissue formation. As described above, an in vitro assay that is representative of the induction of the desired tissue type is preferred at this stage. The assay may monitor mRNA or protein levels as a function of time or at a set time after administration of the morphogenic protein to cells or a tissue explant.

Figure 6:
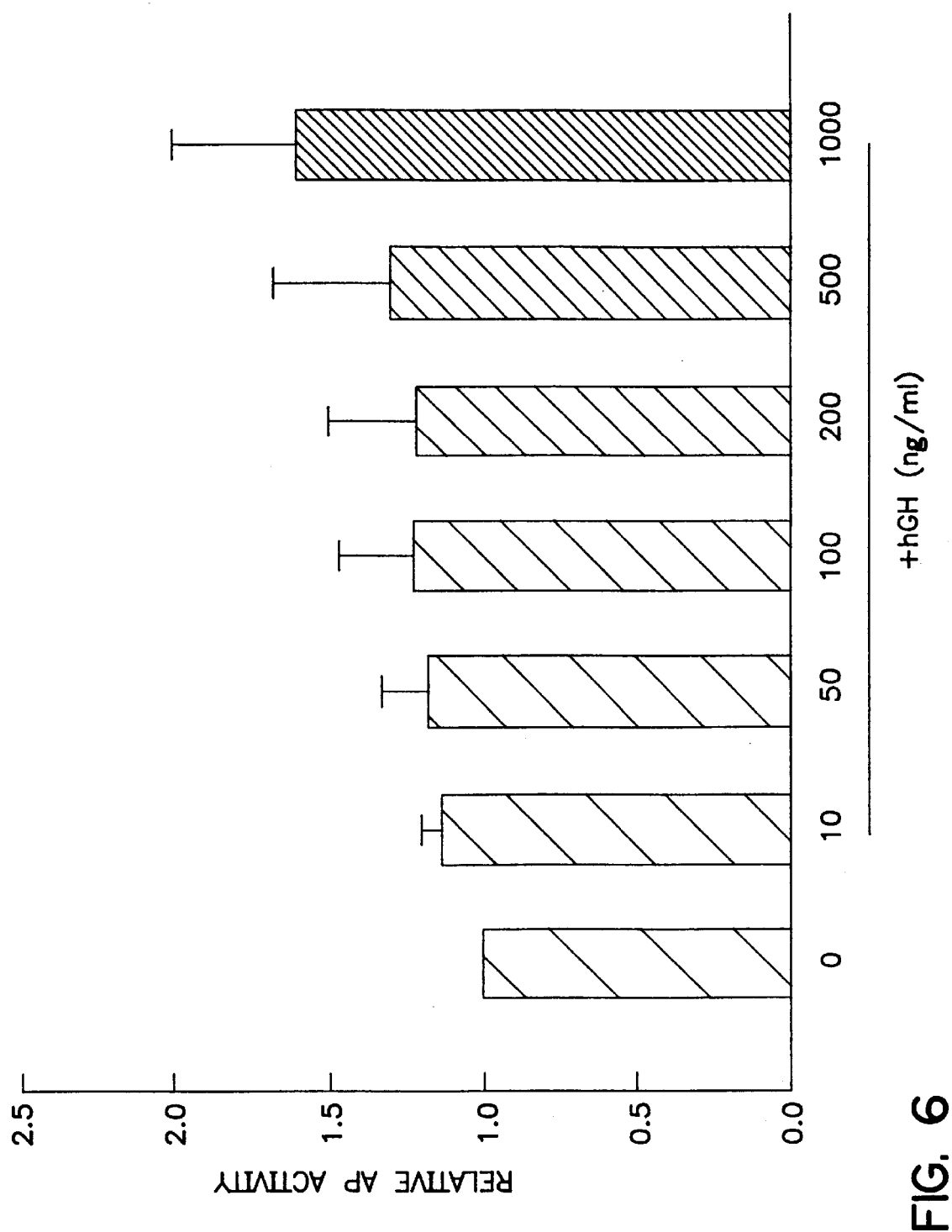
FIG. 6. Growth hormone is a MPSF in concert with OP-1. Alkaline phosphatase (AP) activity (nmol/$\mu$g protein) in FRC cells is indicated. FRC cells were incubated in serum free media containing OP-1 alone (200 ng/ml; "0"), or containing increasing concentrations of hGH (10–100 ng/ml) in the presence of 200 ng/ml OP-1. Control cultures (CON) were grown in serum free media containing solvent vehicles (not shown).
Figure 7:
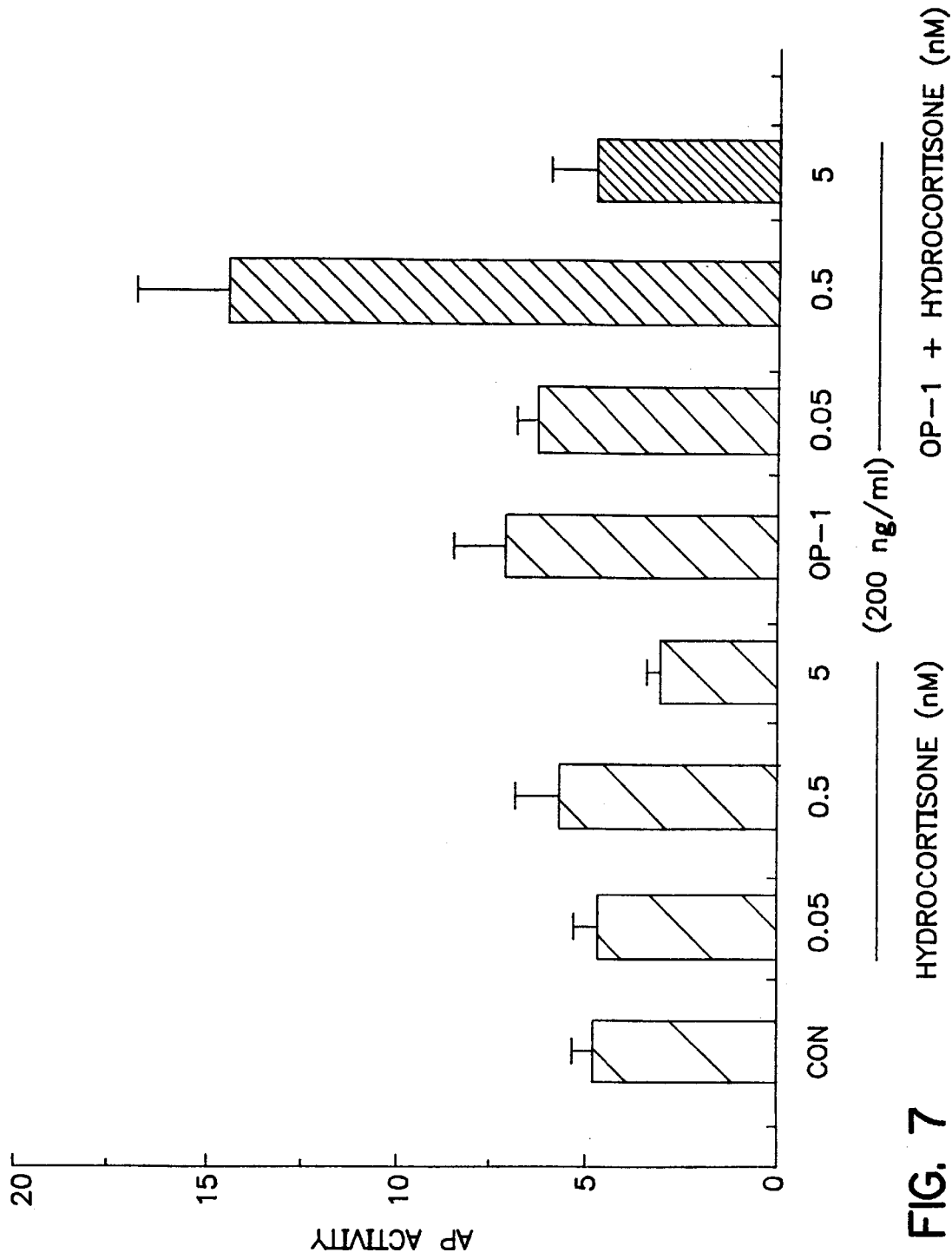
FIG. 7. Hydrocortisone is a MPSF in concert with OP-1. Alkaline phosphatase (AP) activity (nmol/$\mu$g protein) in FRC cells is indicated. FRC cells were incubated in serum free media containing OP-1 alone (200 ng/ml), or containing increasing concentrations of hydrocortisone (0.05, 0.5 and 5.0 nM) in the presence or absence of 200 ng/ml OP-1. Control cultures (CON) were grown in serum free media containing solvent vehicles.
Figure 9:
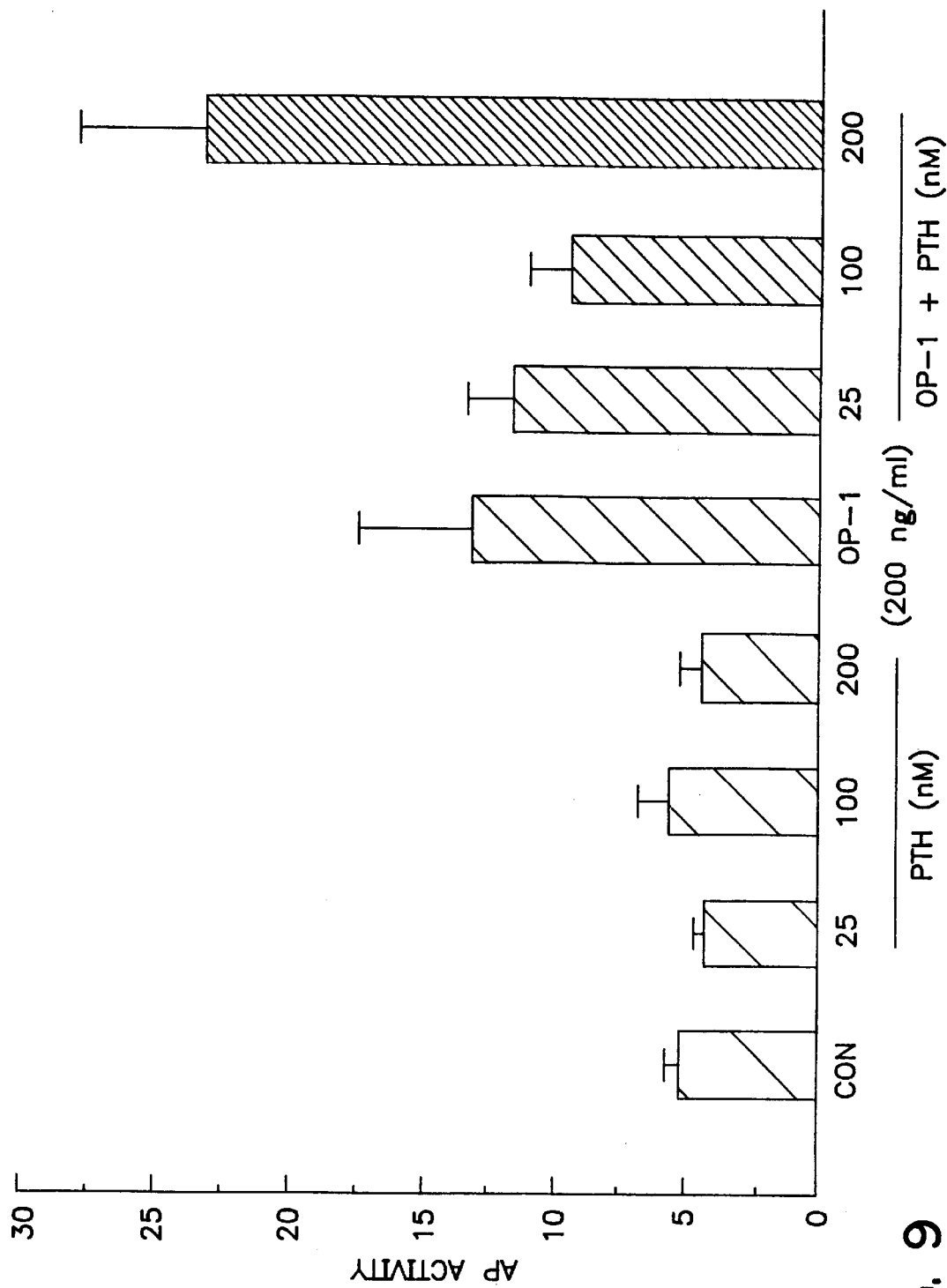
FIG. 9. Parathyroid hormone is a MPSF in concert with OP-1. Alkaline phosphatase (AP) activity (nmol/$\mu$g protein) in FRC cells is indicated. FRC cells were incubated with OP-1 alone (200 ng/ml) and with increasing concentrations of parathyroid hormone (PTH; 25, 100 and 200 ng/ml) in the presence or absence of 200 ng/ml OP-1. Control cultures (CON) were grown in serum free media containing solvent vehicles.
Figure 10:
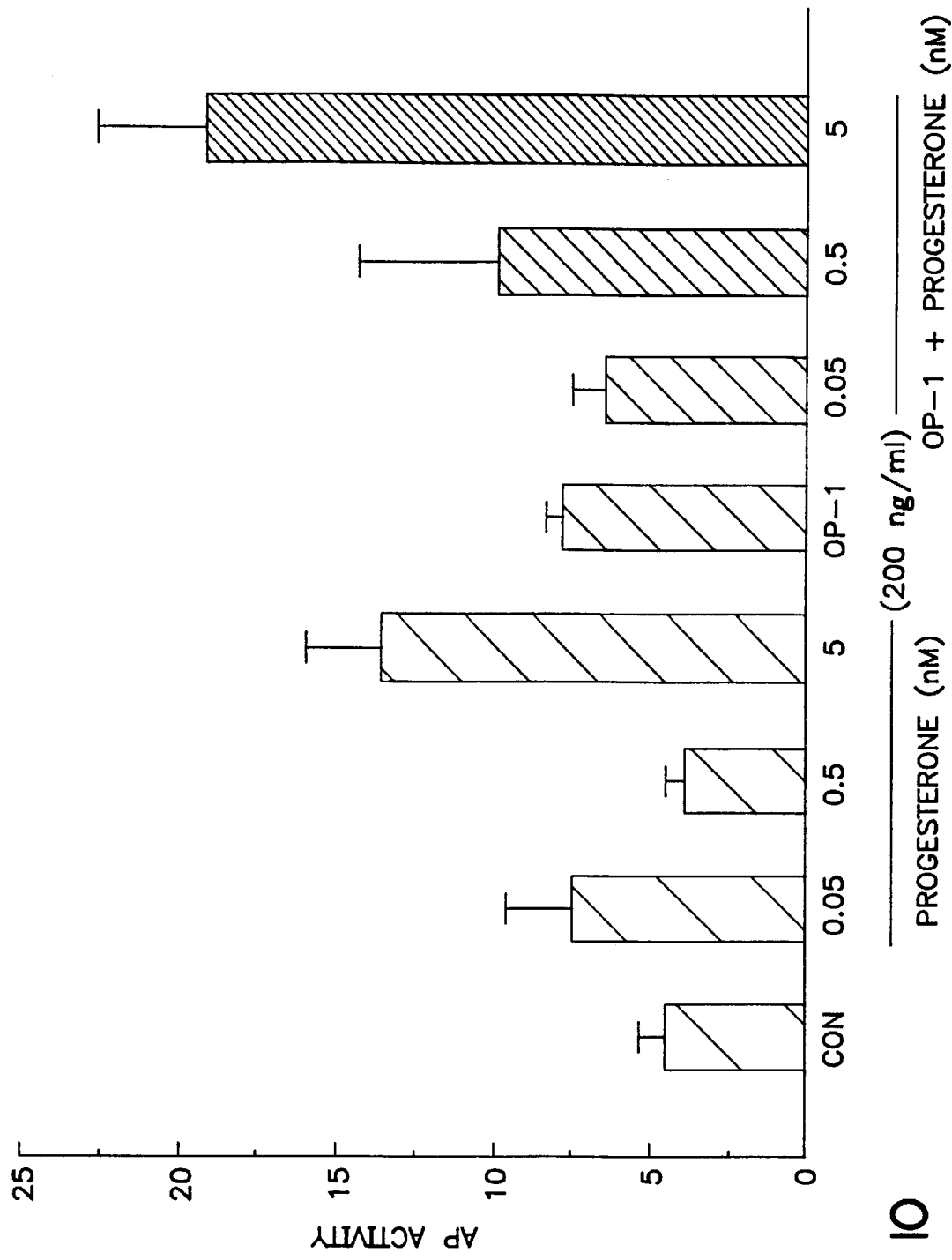
FIG. 10. Progesterone is a MPSF in concert with OP-1. Alkaline phosphatase (AP) activity (nmol/$\mu$g protein) in FRC cells is indicated. FRC cells were incubated with OP-1 alone (200 ng/ml) and with increasing concentrations of progesterone (0.05, 0.5 and 5.0 nM) in the presence or absence of 200 ng/ml OP-1. Control cultures (CON) were grown in serum free media containing solvent vehicles.

As described in Example 4, increasing concentrations of the following compounds were tested as MPSFs in combination with a single concentration (200 ng/ml) of osteogenic protein OP-1: a) estradiol (FIG. 5); b) growth hormone (hGH; FIG. 6); c) hydrocortisone (HC; FIG. 7); d) insulin (FIG. 8); e) parathyroid hormone (PTH; FIG. 9); and f) progesterone (PG; FIG. 10). The results of these experiments demonstrate that each of the above compounds functions within a particular concentration range as an MPSF in combination with OP-1.

In general, at least about 1 ng/ml of morphogenic protein is combined with at least about 0.01 ng/ml of MPSF to observe an increase in the morphogenic activity. Preferred concentration ranges for combinations of osteogenic protein OP-1 and MPSF in inducing bone and cartilage formation, as determined in experiments such as those shown in FIGS. 3 and 5–10, are shown in TABLE 1. It is envisioned that some of the MPSFs, particularly the hormones, may be more effective if also pre-administered to the cells before the OP-1/MPSF composition is applied.

TABLE 1

OP-1/MPSF Preferred Concentration Ranges

| | Morphogenic Protein (ng/ml) | | MPSF |
|---|---|---|---|
| OP-1 | 1–500 | IGF-I | 0.1–50 ng/ml |
| OP-1 | 1–500 | estradiol | 0.05–1000 nM |
| OP-1 | 1–500 | hGH | 5.0–1000 ng/ml |
| OP-1 | 1–500 | HC | 0.05–5.0 nM |
| OP-1 | 1–500 | insulin | 0.01–1000 nM |
| OP-1 | 1–500 | PTH | 10.0–1000 nM |
| OP-1 | 1–500 | PG | 0.05–1000 nM |

Preferred concentration ranges for combinations of osteogenic protein OP-1 and MPSF in inducing bone and cartilage formation are shown in TABLE 2.

TABLE 2

OP-1/MPSF More Preferred Concentrations

| | Morphogenic Protein (ng/ml) | | MPSF |
|---|---|---|---|
| OP-1 | 200 | IGF-I | 25 ng/ml |
| OP-1 | 200 | estradiol | 5 nM |
| OP-1 | 200 | hGH | 500–1000 ng/ml |
| OP-1 | 200 | HC | 0.5–5.0 nM |
| OP-1 | 200 | insulin | 0.05 nM |
| OP-1 | 200 | PTH | 25–200 nM |
| OP-1 | 200 | PG | 0.05–5 nM |

It will be appreciated by those skilled in the art that the preferred concentration range of MPSF in a particular assay may vary depending on the concentration of the morphogenic protein selected. Systematic variation of the relative concentrations of the morphogenic protein and MPSF should thus be performed to optimize concentration ratios of the two factors. This may be done essentially as described in Example 2 and shown in FIG. 3 for OP-1 and IGF-I.

Figure 11:
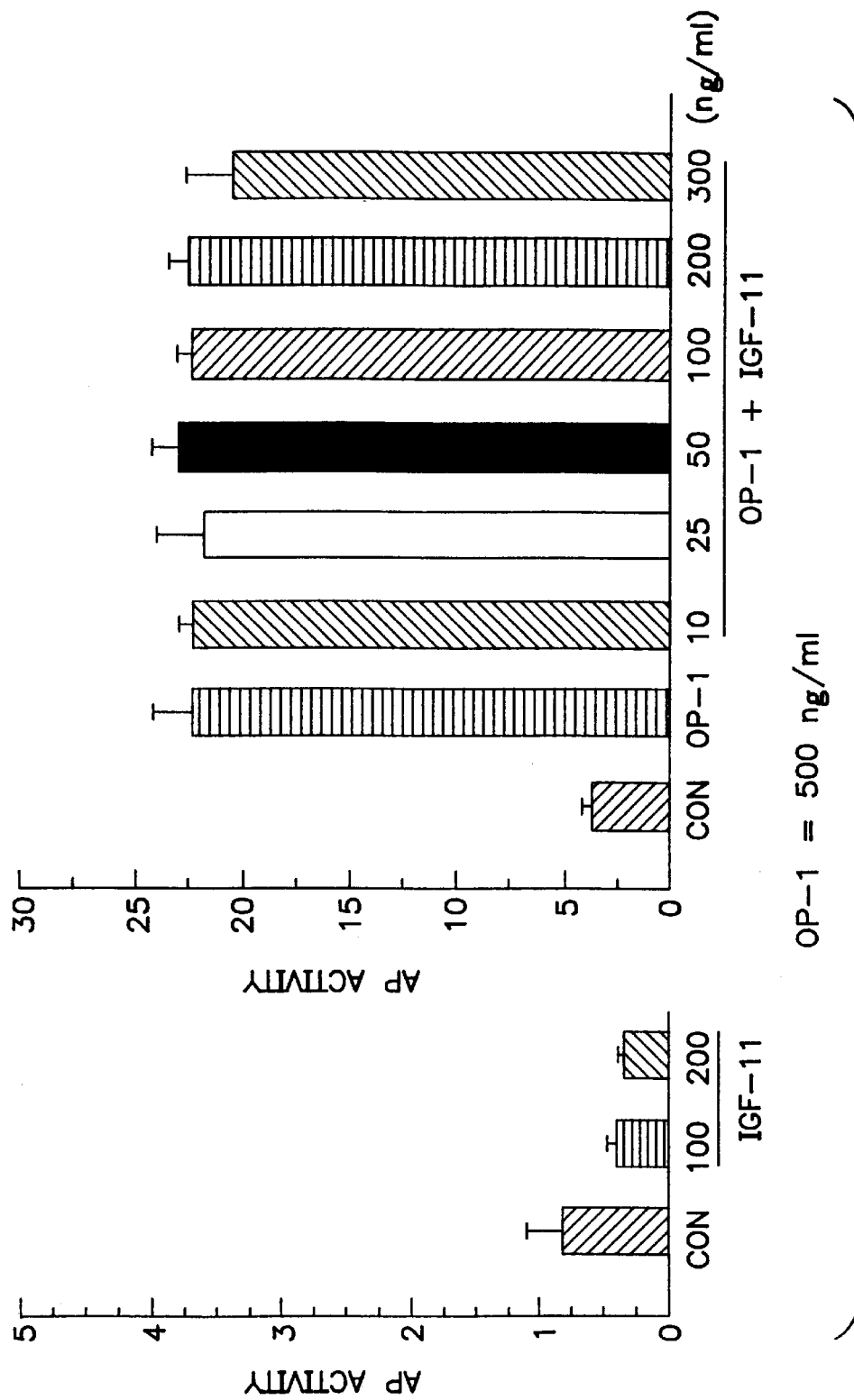
FIG. 11. IGF-II does not stimulate OP-1-induced osteogenic induction. Alkaline phosphatase (AP) activity (nmol/$\mu$g protein) in FRC cells is indicated. FRC cells were incubated with OP-1 alone (500 ng/ml) and with increasing concentrations of IGF-II (10–300 ng/ml) in the presence or absence (shown only for 100 and 200 ng/ml IGF-II) of 500 ng/ml OP-1. Control cultures (CON) were grown in serum free media containing solvent vehicles.

To determine whether other members of the IGF growth factor family also exhibit a synergistic effect with OP-1 similar to that observed for IGF-I, FRC cells were co-incubated with OP-1 (500 ng/ml) and varying concentrations of IGF-II. As shown in FIG. 11, IGF-II (10–300 ng/ml) neither enhanced nor inhibited OP-1-stimulated increase in AP activity. In addition, the level of AP activity in FRC cultures treated with IGF-I (25 ng/ml)+OP-1 (500 ng/ml) was similar to that in cultures treated with IGF-II (25 ng/ml)+IGF-I (25 ng/ml)+OP-1 (500 ng/ml). Thus IGF-II (925 ng/ml) does not further potentiate the synergistic effect that IGF-I has on OP-1-induced tissue formation.

Figure 12:
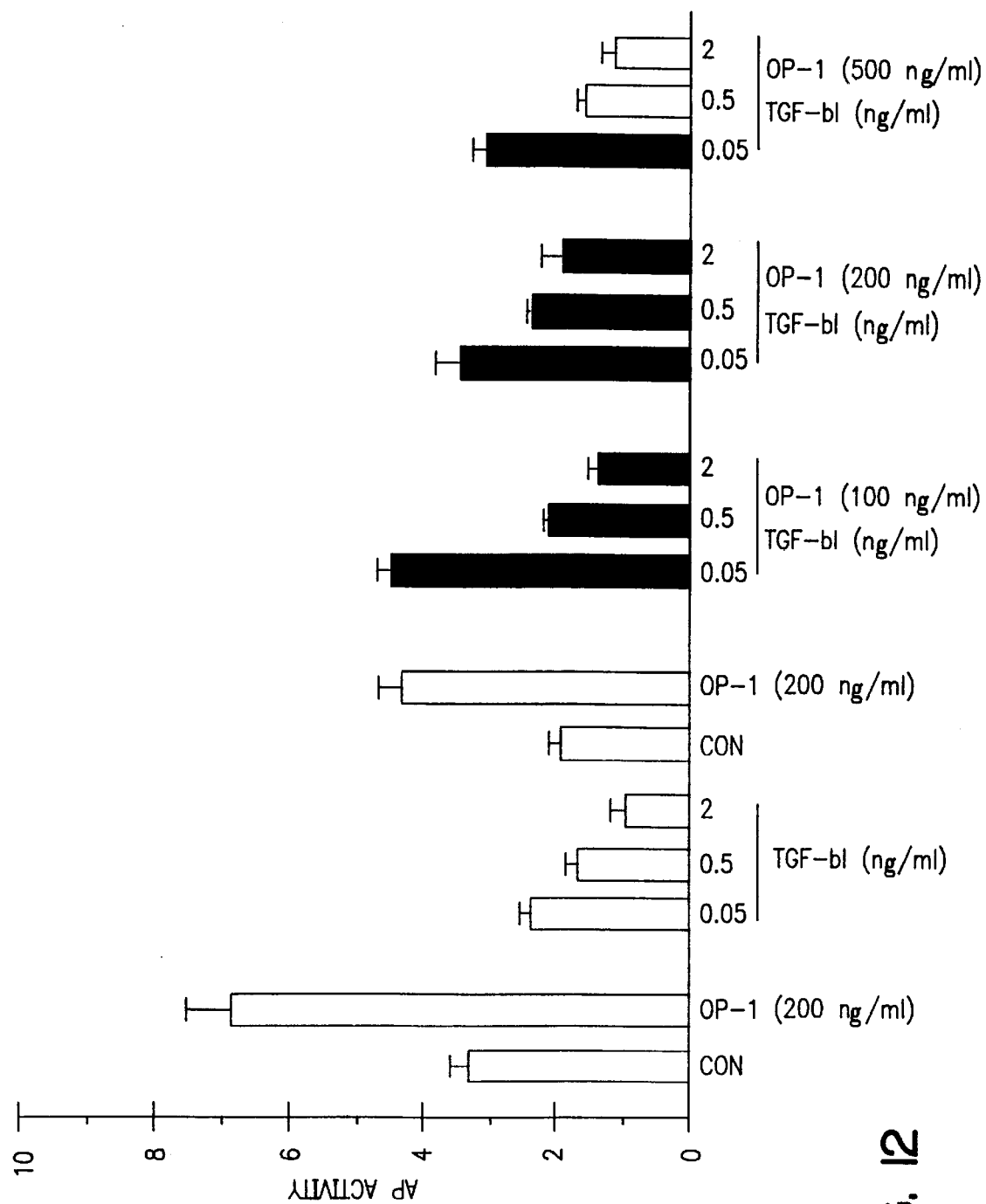
FIG. 12. TGF-$\beta$ does not stimulate OP-1-induced osteogenic induction. Alkaline phosphatase (AP) activity (nmol/$\mu$g protein) in FRC cells is indicated. FRC cells were grown in serum free media containing: OP-1 alone (200 ng/ml), TGF-$\beta$ alone (0.05–2 ng/ml), or containing increasing concentrations of TGF-$\beta$ (0.05–50 ng/ml) in the presence of OP-1 at 100 ng/ml, 200 ng/ml or 500 ng/ml. Control cultures (CON) were grown in serum free media containing solvent vehicles.

The data summarized in FIG. 12 indicate that TGF-β is not a MPSF in combination with OP-1 in the AP activity assay in FRC cells. TGF-β alone did not stimulate AP activity. TGF-β (0.05–3.0 ng/ml) did not exhibit any synergistic effect with OP-1 on AP activity.

Based on morphogenic protein/MPSF dose response curves, compositions comprising a morphogenic protein and a MPSF may be formulated at various concentration ratios and tested in a bioassay selected to represent the tissue inductive activity which will ultimately be used in the tissue treatment. The preferred assay is ultimately an ex vivo or in vivo tissue induction bioassay such as those described in Examples 7–13.

Pharmaceutical Compositions

The pharmaceutical compositions provided by this invention comprise at least one and optionally more than one morphogenic protein/MPSF combinations that are capable of inducing tissue formation when administered or implanted into a patient. The compositions of this invention will be administered at an effective dose to induce the particular type of tissue at the treatment site selected according to the particular clinical condition addressed. Determination of a preferred pharmaceutical formulation and a therapeutically efficient dose regiment for a given application is well within the skill of the art taking into consideration, for example, the administration mode, the condition and weight of the patient, the extent of desired treatment and the tolerance of the patient for the treatment.

Doses expected to be suitable starting points for optimizing treatment regiments are based on the results of in vitro assays (e.g., Examples 3–5), and ex vivo or in vivo assays (e.g., Examples 7–13). Based on the results of such assays, a range of suitable morphogenic protein and MPSF concentration ratios can be selected to test at a treatment site in animals and then in humans.

Administration of the morphogenic proteins and MPSFs of this invention, including isolated and purified forms of morphogenic protein complexes, their salts or pharmaceutically acceptable derivatives thereof, may be accomplished using any of the conventionally accepted modes of administration of agents which exhibit immunosuppressive activity.

The pharmaceutical compositions comprising a morphogenic protein and a MPSF of this invention may be in a variety of forms. These include, for example, solid, semi-solid and liquid dosage forms such as tablets, pills, powders, liquid solutions or suspensions, suppositories, and injectable and infusible solutions. The preferred form depends on the intended mode of administration and therapeutic application and may be selected by one skilled in the art. Modes of administration may include oral, parenteral, subcutaneous, intravenous, intralesional or topical administration. In most cases, the pharmaceutical compositions of this invention will be administered in the vicinity of the treatment site in need of tissue regeneration or repair.

The pharmaceutical compositions comprising a morphogenic protein and a MPSF of this invention may, for example, be placed into sterile, isotonic formulations with or without cofactors which stimulate uptake or stability. The formulation is preferably liquid, or may be lyophilized powder. For example, the morphogenic protein and MPSF of this invention may be diluted with a formulation buffer comprising 5.0 mg/ml citric acid monohydrate, 2.7 mg/ml trisodium citrate, 41 mg/ml mannitol, 1 mg/ml glycine and 1 mg/ml polysorbate 20. This solution can be lyophilized, stored under refrigeration and reconstituted prior to administration with sterile Water-For-Injection (USP).

The compositions also will preferably include conventional pharmaceutically acceptable carriers well known in the art (see for example Remington's Pharmaceutical Sciences, 16th Edition, 1980, Mac Publishing Company). Such pharmaceutically acceptable carriers may include other medicinal agents, carriers, genetic carriers, adjuvants, excipients, etc., such as human serum albumin or plasma preparations. The compositions are preferably in the form of a unit dose and will usually be administered as a dose regiment that depends on the particular tissue treatment.

The pharmaceutical compositions of this invention may also be administered in conjunction with a morphogenic device using, for example, microspheres, liposomes, other microparticulate delivery systems or sustained release formulations placed in, near, or otherwise in communication with affected tissues or the bloodstream bathing those tissues (see morphogenic devices, below).

Liposomes containing a morphogenic protein and a MPSF of this invention can be prepared by well-known methods (See, e.g. DE 3,218,121; Epstein et al., *Proc. Natl. Acad. Sci. U.S.A.*, 82, pp. 3688–92 (1985); Hwang et al., *Proc. Natl. Acad. Sci. U.S.A.*, 77, pp. 4030–34 (1980); U.S. Pat. Nos. 4,485,045 and 4,544,545). Ordinarily the liposomes are of the small (about 200–800 Angstroms) unilamellar type in which the lipid content is greater than about 30 mol. % cholesterol. The proportion of cholesterol is selected to control the optimal rate of morphogenic protein and MPSF release.

The morphogenic proteins and MPSFs of this invention may also be attached to liposomes containing other biologically active molecules such as immunosuppressive agents, cytokines, etc., to modulate the rate and characteristics of tissue induction. Attachment of morphogenic proteins and MPSFs to liposomes may be accomplished by any known cross-linking agent such as heterobifunctional cross-linking agents that have been widely used to couple toxins or chemotherapeutic agents to antibodies for targeted delivery. Conjugation to liposomes can also be accomplished using the carbohydrate-directed cross-linking reagent 4-(4-maleimidophenyl) butyric acid hydrazide (MPBH) (Duzgunes et al., *J. Cell. Biochem. Abst.* Suppl. 16E 77 (1992)).

Morphogenic Devices

The morphogenic devices of this invention comprise a morphogenic protein and at least one MPSF dispersed in an implantable biocompatible carrier material that functions as a suitable delivery or support system for the compounds. Suitable examples of sustained release carriers include semipermeable polymer matrices in the form of shaped articles such as suppositories or capsules. Implantable or microcapsular sustained release matrices include polylactides (U.S. Pat. No. 3,773,319; EP 58,481), copolymers of L-glutamic acid and ethyl-L-glutamate (Sidman et al., *Biopolymers*, 22, pp. 547–56 (1985)); poly(2-hydroxyethyl-methacrylate) or ethylene vinyl acetate (Langer et al., *J. Biomed. Mater. Res.*, 15, pp. 167–277 (1981); Langer, *Chem. Tech.*, 12, pp. 98–105 (1982)).

In one embodiment of this invention, the carrier of the morphogenic device comprises a biocompatible matrix made up of particles or porous materials. The pores are preferably of a dimension to permit progenitor cell migration and subsequent differentiation and proliferation. Various matrices known in the art can be employed (see, e.g., U.S. Pat. Nos. 4,975,526; 5,162,114; 5,171,574 and WO 91/18558, which are herein incorporated by reference).

The particle size should be within the range of 70 $\mu$m–850 $\mu$m, preferably 70 $\mu$m–420 $\mu$m, most preferably 150 $\mu$m–420 $\mu$m. The matrix may be fabricated by close packing particulate material into a shape spanning the particular tissue defect to be treated. Alternatively, a material that is biocompatible, and preferably biodegradable in vivo may be structured to serve as a temporary scaffold and substratum for recruitment of migratory progenitor cells, and as a base for their subsequent anchoring and proliferation.

Useful matrix materials comprise, for example, collagen; homopolymers or copolymers of glycolic acid, lactic acid, and butyric acid, including derivatives thereof; and ceramics, such as hydroxyapatite, tricalcium phosphate and other calcium phosphates. Various combinations of these or other suitable matrix materials also may be useful as determined by the assays set forth herein.

Currently preferred carriers include particulate, demineralized, guanidine-extracted, species-specific (allogenic) bone, and specially treated particulate, protein-extracted, demineralized xenogenic bone (Example 6). Optionally, such xenogenic bone powder matrices also may be treated with proteases such as trypsin. Preferably, the xenogenic matrices are treated with one or more fibril modifying agents to increase the intraparticle intrusion volume (porosity) and surface area. Useful modifying agents include solvents such as dichloromethane, trichloroacetic acid, acetonitrile and acids such as trifluoroacetic acid and hydrogen fluoride. The currently preferred fibril-modifying agent useful in formulating the matrices of this invention is a heated aqueous medium, preferably an acidic aqueous medium having a pH less than about pH 4.5, most preferably having a pH within the range of about pH 2–pH 4. A currently preferred heated acidic aqueous medium is 0.1% acetic acid which has a pH of about 3. Heating demineralized, delipidated, guanidine-extracted bone collagen in an aqueous medium at elevated temperatures (e.g., in the range of about 37° C.–65° C., preferably in the range of about 45° C.–60° C.) for approximately one hour generally is sufficient to achieve the desired surface morphology. Although the mechanism is not clear, it is hypothesized that the heat treatment alters the collagen fibrils, resulting in an increase in the particle surface area.

Demineralized guanidine-extracted xenogenic bovine bone comprises a mixture of additional materials that may be fractionated further using standard biomolecular purification techniques. For example, chromatographic separation of extract components followed by addition back to active matrix of the various extract fractions corresponding to the chromatogram peaks may be used to improve matrix properties by fractionating away inhibitors of bone or tissue-inductive activity.

The matrix may also be substantially depleted in residual heavy metals. Treated as disclosed herein, individual heavy metal concentrations in the matrix can be reduced to less than about 1 ppm.

One skilled in the art may create a biocompatible matrix of choice having a desired porosity or surface microtexture useful in the production of morphogenic devices to promote bone or other tissue induction, or as a biodegradable sustained release implant. In addition, synthetically formulated matrices, prepared as disclosed herein, may be used.

General Consideration of Matrix Properties

The currently preferred carrier material is a xenogenic bone-derived particulate matrix treated as described herein. This carrier may be replaced by either a biodegradable-synthetic or a synthetic-inorganic matrix (e.g., hydroxyapatite (HAP), collagen, carboxymethyl-cellulose, tricalcium phosphate or polylactic acid, polyglycolic acid, polybutyric acid and various copolymers thereof.)

Matrix geometry, particle size, the presence of surface charge, and the degree of both intra- and inter-particle porosity are all important to successful matrix performance. Studies have shown that surface charge, particle size, the presence of mineral, and the methodology for combining matrix and morphogenic proteins all play a role in achieving successful tissue induction.

For example, in bone formation using osteogenic protein OP-1 and a MPSF, perturbation of the matrix charge by chemical modification can abolish bone inductive responses. Particle size influences the quantitative response of new bone; particles between 70 $\mu$m and 420 $\mu$m elicit the maximum response. Contamination of the matrix with bone mineral will inhibit bone formation. Most importantly, the procedures used to formulate osteogenic protein and MPSF onto the matrix are extremely sensitive to the physical and chemical state of both the proteins and the matrix.

The sequential cellular reactions in the interface of the bone matrix/osteogenic protein implants are complex. The multistep cascade includes: binding of fibrin and fibronectin to implanted matrix, migration and proliferation of mesenchymal cells, differentiation of the progenitor cells into chondroblasts, cartilage formation, cartilage calcification, vascular invasion, bone formation, remodeling, and bone marrow differentiation.

A successful carrier for morphogenic protein and MPSF should perform several important functions. It should act as a slow release delivery system of morphogenic protein and MPSF, protect the morphogenic protein and MPSF from non-specific proteolysis, and should accommodate each step of the cellular responses involved in progenitor cell induction during tissue development.

In addition, selected materials must be biocompatible in vivo and preferably biodegradable; the carrier preferably acts as a temporary scaffold until replaced completely by new bone or tissue. Polylactic acid (PLA), polyglycolic acid (PGA), and various combinations have different dissolution rates in vivo. In bones, the dissolution rates can vary according to whether the implant is placed in cortical or trabecular bone.

The preferred osteogenic device matrix material, prepared from xenogenic bone and treated as disclosed herein, produces an implantable material useful in a variety of clinical settings. In addition to its use as a matrix for bone formation in various orthopedic, periodontal, and reconstructive procedures, the matrix also may be used as a sustained release carrier, or as a collagenous coating for orthopedic or general prosthetic implants.

The matrix may be shaped as desired in anticipation of surgery or shaped by the physician or technician during surgery. It is preferred to shape the matrix to span a tissue defect and to take the desired form of the new tissue. In the case of bone repair of a non-union defect, for example, it is desirable to use dimensions that span the non-union. Rat studies show that the new bone is formed essentially having the dimensions of the device implanted. Thus, the material may be used for topical, subcutaneous, intraperitoneal, or intramuscular implants. In bone formation procedures, the material is slowly absorbed by the body and is replaced by bone in the shape of or very nearly the shape of the implant.

The matrix may comprise a shape-retaining solid made of loosely-adhered particulate material, e.g., collagen. It may also comprise a molded, porous solid, or simply an aggregation of close-packed particles held in place by surrounding tissue. Masticated muscle or other tissue may also be used. Large allogenic bone implants can act as a carrier for the matrix if their marrow cavities are cleaned and packed with particles comprising dispersed osteogenic protein and MPSF. The matrix may also take the form of a paste or a hydrogel.

When the carrier material comprises a hydrogel matrix, it refers to a three dimensional network of cross-linked hydrophilic polymers in the form of a gel substantially composed of water, preferably but not limited to gels being greater than 90% water. Hydrogel matrices can carry a net positive or net negative charge, or may be neutral. A typical net negative charged matrix is alginate. Hydrogels carrying a net positive charge may be typified by extracellular matrix components such as collagen and laminin. Examples of commercially available extracellular matrix components include Matrigel™ and Vitrogen™. An example of a net neutral hydrogel is highly crosslinked polyethylene oxide, or polyvinylalcohol.

Various growth factors, cytokines, hormones, trophic agents and therapeutic compositions including antibiotics and chemotherapeutic agents, enzymes, enzyme inhibitors and other bioactive agents also may be adsorbed onto or dispersed within the carrier material comprising the morphogenic protein and MPSF, and will also be released over time at the implantation site as the matrix material is slowly absorbed.

Other Tissue-Specific Matrices

In addition to the naturally-derived bone matrices described above, useful matrices may also be formulated synthetically by adding together reagents that have been appropriately modified. One example of such a matrix is the porous, biocompatible, in vivo biodegradable synthetic matrix disclosed in WO91/18558, the disclosure of which is hereby incorporated by reference.

Briefly, the matrix comprises a porous crosslinked structural polymer of biocompatible, biodegradable collagen, most preferably tissue-specific collagen, and appropriate, tissue-specific glycosaminoglycans as tissue-specific cell attachment factors. Bone tissue-specific collagen (e.g., Type I collagen) derived from a number of sources may be suitable for use in these synthetic matrices, including soluble collagen, acid-soluble collagen, collagen soluble in neutral or basic aqueous solutions, as well as those collagens which are commercially available. In addition, Type II collagen, as found in cartilage, also may be used in combination with Type I collagen.

Glycosaminoglycans (GAGs) or mucopolysaccharides are polysaccharides made up of residues of hexoamines glycosidically bound and alternating in a more-or-less regular manner with either hexouronic acid or hexose moieties. GAGs are of animal origin and have a tissue specific distribution (see, e.g., Dodgson et al., in *Carbohydrate Metabolism and its Disorders,* Dickens et al., eds., Vol. 1, Academic Press (1968)). Reaction with the GAGs also provides collagen with another valuable property, i.e., inability to provoke an immune reaction (foreign body reaction) from an animal host.

Useful GAGs include those containing sulfate groups, such as hyaluronic acid, heparin, heparin sulfate, chondroitin 6-sulfate, chondroitin 4-sulfate, dermatan sulfate, and keratin sulfate. For osteogenic devices, chondroitin 6-sulfate currently is preferred. Other GAGs also may be suitable for forming the matrix described herein, and those skilled in the art will either know or be able to ascertain other suitable GAGs using no more than routine experimentation. For a more detailed description of mucopolysaccharides, see Aspinall, Polysaccharides, Pergamon Press, Oxford (1970).

Collagen can be reacted with a GAG in aqueous acidic solutions, preferably in diluted acetic acid solutions. By adding the GAG dropwise into the aqueous collagen dispersion, coprecipitates of tangled collagen fibrils coated with GAG results. This tangled mass of fibers then can be homogenized to form a homogeneous dispersion of fine fibers and then filtered and dried.

Insolubility of the collagen-GAG products can be raised to the desired degree by covalently cross-linking these materials, which also serves to raise the resistance to resorption of these materials. In general, any covalent G60 cross-linking method suitable for cross-linking collagen also is suitable for cross-linking these composite materials, although cross-linking by a dehydrothermal process is preferred.

When dry, the cross-linked particles are essentially spherical with diameters of about 500 $\mu$m. Scanning electron microscopy shows pores of about 20 $\mu$m on the surface and 40 $\mu$m on the interior. The interior is made up of both fibrous and sheet-like structures, providing surfaces for cell attachment. The voids interconnect, providing access to the cells throughout the interior of the particle. The material appears to be roughly 99.5% void volume, making the material very efficient in terms of the potential cell mass that can be grown per gram of microcarrier.

Another useful synthetic matrix is one formulated from biocompatible, in vivo biodegradable synthetic polymers, such as those composed of glycolic acid, lactic acid and/or butyric acid, including copolymers and derivatives thereof. These polymers are well described in the art and are available commercially. For example, polymers composed of polylactic acid (e.g., MW 100 ka), 80% polylactide/20% glycoside or poly 3-hydroxybutyric acid (e.g., MW 30 ka) all may be purchased from PolySciences, Inc. The polymer compositions generally are obtained in particulate form and the morphogenic devices preferably fabricated under non-aqueous conditions (e.g., in an ethanol-trifluoroacetic acid solution, EtOH/TFA) to avoid hydrolysis of the polymers. In addition, one can alter the morphology of the particulate polymer compositions, for example to increase porosity, using any of a number of particular solvent treatments known in the art.

Fabrication of morphogenic device

The naturally-sourced, synthetic and recombinant morphogenic proteins and MPSFs as set forth above, as well as other constructs, can be combined and dispersed in a suitable matrix preparation using any of the methods described. In general, about 500–1000 ng of active morphogenic protein and about 10–200 ng of an active MPSF are combined with 25 mg of the inactive carrier matrix for rat bioassays. In larger animals, typically about 0.8–1 mg of active morphogenic protein per gram of carrier is combined with 100 ng or more of an active MPSF. The optimal ratios of morphogenic protein to MPSF for a specific combination and tissue type may be determined empirically by those of skill in the art according to the procedures set forth herein. Greater amounts may be used for large implants.

Prosthetic Devices

In another embodiment of this invention, an implantable prosthetic device comprising an osteogenic protein and a MPSF is provided. Any prosthetic implant selected for a particular treatment by the skilled practitioner may be used in combination with a composition comprising at least one osteogenic protein and at least one MPSF according to this invention. The prosthesis may be made from a material comprising metal or ceramic. Preferred prosthetic devices are selected from the group consisting of a hip device, a screw, a rod and a titanium cage for spine fusion.

The osteogenic composition is disposed on the prosthetic implant on a surface region that is implantable adjacent to a target tissue in the mammal. Preferably, the mammal is a human patient. The composition is disposed on the surface of the implant in an amount sufficient to promote enhanced tissue growth into the surface. The amount of the composition sufficient to promote enhanced tissue growth may be determined empirically by those of skill in the art using bioassays such as those described herein and in Rueger et al., U.S. Pat. No. 5,344,654, which is incorporated herein by reference. Preferably, animal studies are performed to optimize the concentration of the composition components before a similar prosthetic device is used in the human patient. Such prosthetic devices will be useful for repairing orthopedic defects, injuries or anomalies in the treated mammal.

Thus this invention also provides a method for promoting in vivo integration of an implantable prosthetic device into a target tissue of a mammal comprising the steps of providing on a surface of the prosthetic device a composition comprising at least one osteogenic protein and at least one MPSF, and implanting the device in a mammal at a locus where the target tissue and the surface of the prosthetic device are maintained at least partially in contact for a time sufficient to permit enhanced tissue growth between the target tissue and the device.

Bioassays

The various morphogenic compositions and devices of this invention are preferably evaluated with ex vivo or in vivo bioassays. Studies in rats show the osteogenic effect in an appropriate matrix to be dependent on the dose of morphogenic protein dispersed in the matrix. No activity is observed if the matrix is implanted alone. In vivo bioassays performed in the rat model also have shown that demineralized, guanidine- extracted xenogenic bone matrix materials of the type described in the literature generally are ineffective as a carrier, can fail to induce bone, and can produce an inflammatory and immunological response when implanted unless treated as disclosed above. In certain species (e.g., monkey), allogenic matrix materials also apparently are ineffective as carriers (Aspenberg et al., *J. Bone Joint Surgery*, 70, pp. 625–627 (1988)). Examples 6–13 set forth various procedures for preparing morphogenic devices and for evaluating their morphogenic utility using in vivo mammalian bioassays.

A rat bioassay for bone induction—based on the bioassay for induction of bone differentiation activity as described by Sampath and Reddi (*Proc. Natl. Acad. Sci. USA*, 80, pp. 6591–95 (1983)), herein incorporated by reference—may be used to monitor osteogenic activity of osteogenic proteins in concert with one or more MPSFs (Example 7). Rat bioassays are preferred as the first step in moving from in vitro assay results to in vivo implantation studies.

The feline and rabbit as established large animal efficacy models for osteogenic device testing have been described in detail (Oppermann et al., U.S. Pat. No. 5,354,557; Example 8 and Example 9). The feline femoral model, the rabbit ulnar model, the dog ulnar model (Example 10) or the monkey model (Example 11) are all useful assays to evaluate whether the compositions and devices of this invention comprising one or more osteogenic proteins in combination with one or more MPSFs can enhance bone regeneration in vivo and for determining optimal dosing of morphogenic protein/MPSF combinations.

Preferably, results from the rat bioassay (Example 7) are used as a starting point for optimization studies in one of these larger animal models. Most preferably, the larger animal study is performed in the dog or the monkey.

While the feline and the rabbit studies use allogenic matrices as osteogenic device carrier material, appropriate treatment as described herein of any bone-derived or synthetic matrix material is anticipated to render the matrix suitable for xenogenic implants. However, results in the rabbit tend to be less predictable when using osteogenic proteins (with or without MPSFs) dispersed in bovine-derived collagen matrix.

Recombinant BMP-2 is effective in repairing large bone defects in a variety of other mammalian bioassay models. Implanted osteogenic devices comprising BMP-2 successfully heal segmental defects in rat femurs (Yasko et al., *J. Bone Joint Sura.*, 74A, pp. 659–70 (1992), sheep femurs (Gerhart et al., *Clin. Orthop.*, 293, pp. 317–26 (1993), in canine mandibles (Toriumi et al., *Arch. Otolaryngol. Head Neck Surg.*, 117, pp. 1101–12 (1991), and in skull defects in rats and dogs.

The procedures described above may be used to assess the ability of one or more MPSFs to enhance the osteogenic activity of one or more osteogenic proteins in bone and/or cartilage regeneration and repair in vivo. These procedures may also be used to optimize conditions for enhancing osteogenic activity using one or more MPSFs. It is anticipated that the efficacy of any osteogenic protein/MPSF combination may be characterized using these assays. Various osteogenic protein/MPSF combinations, dose-response curves, various naturally-derived or synthetic matrices, and any other desired variations on the osteogenic device components may be tested using the procedures essentially as described.

Tendon/ligament-like tissue formation bioassay

A modified version of the Sampath and Reddi rat ectopic implant assay (see above) has been reported by Celeste et al., WO 95/16035, which is hereby incorporated by reference. The modified assay monitors tendon and ligament-like tissue formation induced by morphogenic proteins (such as BMP-12, BMP-13 and human MP52). This tendon/ligament-like tissue assay may be used to identify MPSFs that stimulate tendon/ligament-like tissue formation by BMP-12, BMP-13 or other morphogenic proteins in a particular treatment site (Example 12). The assay may also be used to optimize concentrations and treatment schedules for therapeutic tissue repair regiments.

It should be understood that the above experimental procedure may be modified within the skill of the art in a number of ways to be useful in determining whether a morphogenic device is capable of inducing tendon and/or ligament-like tissue in vivo. It may be used to test various combinations of morphogenic protein/MPSF combinations, and to produce an in vivo dose response curve useful in determining effective relative concentrations of morphogenic proteins and MPSFs. It may also be used for identifying concentration ranges in which a particular MPSF may additively or synergistically enhance the inductive activity of a particular morphogenic protein.

The osteogenic proteins BMP-4 and BMP-7 (OP-1) can induce ventral neural plate explants to undergo differentiation into dorsal neural cell fates (Liem et al., *Cell*, 82, pp. 969–79 (1995)). Molecular markers of dorsal cell differentiation are described in Liem et al. These markers include PAX3 and MSX, whose expression delineates an early stage of neural plate cell differentiation; DSL-1 (a BMP-like molecule) delineating differentiation of dorsal neural plate cells at a stage after neural tube closure; and SLUG protein, whose expression after neural tube closure defines premigratory neural crest cells. Expression of these dorsal markers can be induced in ventral neural plate explants by ectopic BMP4 and BMP-7 (OP-1).

A peripheral nerve regeneration assay using the morphogenic protein BMP-2 has been described (Wang et al., WO 95/05846, which is hereby incorporated by reference). The assay involves the implantation of neurogenic devices in the vicinity of severed sciatic nerves in rats. This procedure may be used to assess the ability of a putative MPSF to stimulate the neuronal inducing activity of homo- and heterodimers of morphogenic proteins having neurogenic activity, such as BMP-2, BMP-4, BMP-6 and OP-1 (BMP-7), or of any other selected neurogenic protein/MPSF combinations (Example 13).

Utility of Morphogenic Compositions and Devices

The morphogenic compositions and devices comprising a morphogenic protein and MPSF disclosed herein will permit the physician to treat a variety of tissue injuries, tissue degenerative or disease conditions and disorders that can be ameliorated or remedied by localized, stimulated tissue regeneration or repair.

The morphogenic devices of this invention may be used to induce local tissue formation from a progenitor cell in a mammal by implanting the device at a locus accessible to at least one progenitor cell of the mammal. The morphogenic devices of this invention may be used alone or in combination with other therapies for tissue repair and regeneration.

The morphogenic devices of this invention may also be implanted in or surrounding a joint for use in cartilage and soft tissue repair, or in or surrounding nervous system-associated tissue for use in neural regeneration and repair.

The tissue specificity of the particular morphogenic protein—or combination of morphogenic proteins with other biological factors—will determine the cell types or tissues that will be amenable to such treatments and can be selected by one skilled in the art. The ability to enhance morphogenic protein-induced tissue regeneration by co-administering a MPSF according to the present invention is thus not believed to be limited to any particular cell-type or tissue. It is envisioned that the invention as disclosed herein can be practiced to enhance the activities of new morphogenic proteins and to enhance new tissue inductive functions as they are discovered in the future.

The osteogenic compositions and devices comprising an osteogenic protein and a MPSF will permit the physician to obtain predictable bone and/or cartilage formation using less osteogenic protein to achieve at least about the same extent of bone or cartilage formation. The osteogenic compositions and devices of this invention may be used to treat more efficiently and/or effectively all of the injuries, anomalies and disorders that have been described in the prior art of osteogenic devices. These include, for example, forming local bone in fractures, non-union fractures, fusions and bony voids such as those created in tumor resections or those resulting from cysts; treating acquired and congenital craniofacial and other skeletal or dental anomalies (see e.g., Glowacki et al., Lancet, 1, pp. 959–63 (1981)); performing dental and periodontal reconstructions where lost bone replacement or bone augmentation is required such as in a jaw bone; and supplementing alveolar bone loss resulting from periodontal disease to delay or prevent tooth loss (see e.g., Sigurdsson et al., J. Periodontol., 66, pp. 511–21 (1995)).

An osteogenic device of this invention which comprises a matrix comprising allogenic bone may also be implanted at a site in need of bone replacement to accelerate allograft repair and incorporation in a mammal.

Another potential clinical application of the improved osteogenic devices of this invention is in cartilage repair, for example, following joint injury or in the treatment of osteoarthritis. The ability to enhance the cartilage-inducing activity of morphogenic proteins by co-administering a MPSF may permit faster or more extensive tissue repair and replacement using the same or lower levels of morphogenic proteins.

The morphogenic compositions and devices of this invention will be useful in treating certain congenital diseases and developmental abnormalities of cartilage, bone and other tissues. For example, homozygous OP-1 (BMP-7)-deficient mice die within 24 hours after birth due to kidney failure (Luo et al., J. Bone Min. Res., 10 (Supp. 1), pp. S163 (1995)). Kidney failure in these mice is associated with the failure to form renal glomeruli due to lack of mesenchymal tissue condensation. OP-1-deficient mice also have various skeletal abnormalities associated with their hindlimbs, rib cage and skull, are polydactyl, and exhibit aberrant retinal development. These results, in combination with those discussed above concerning the ability of OP-1 to induce differentiation into dorsal neural cell fates, indicate that OP-1 plays an important role in epithelial-mesenchymal interactions during development. It is anticipated that the compositions, devices and methods of this invention may be useful in the future for ameliorating these and other developmental abnormalities.

Developmental abnormalities of the bone may affect isolated or multiple regions of the skeleton or of a particular supportive or connective tissue type. These abnormalities often require complicated bone transplantation procedures and orthopedic devices. The tissue repair and regeneration required after such procedures may occur more quickly and completely with the use of morphogenic proteins used in combination with MPSFs according to this invention.

Examples of heritable conditions, including congenital bone diseases, for which use of the morphogenic compositions and devices of this invention will be useful include osteogenesis imperfecta, the Hurler and Marfan syndromes, and several disorders of epiphyseal and metaphyseal growth centers such as is presented in hypophosphatasia, a deficiency in alkaline phosphatase enzymatic activity.

Inflammatory joint diseases may also benefit from the improved morphogenic compositions and devices of this invention. These include but are not limited to infectious, non-infectious, rheumatoid and psoriatic arthritis, bursitis, ulcerative colitis, regional enteritis, Whipple's disease, and ankylosing spondylitis (also called Marie Strümpell or Bechterew's disease); the so-called "collagen diseases" such as systemic lupus erythematosus (SLE), progressive systemic sclerosis (scleroderma), polymyositis (dermatomyositis), necrotizing vasculitides, Sjögren's syndrome (sicca syndrome), rheumatic fever, amyloidosis, thrombotic thrombocytopenic purpura and relapsing polychondritis. Heritable disorders of connective tissue include Marfan's syndrome, homocystinuria, Ehlers-Danlos syndrome, osteogenesis imperfecta, alkaptonuria, pseudoxanthoma elasticum, cutis laxa, Hurler's syndrome, and myositis ossificans progressiva.

The following are examples which illustrate the morphogenic compositions and devices of this invention, and methods used to characterize them. These examples should not be construed as limiting: the examples are included for purposes of illustration and the present invention is limited only by the claims.

EXAMPLE 1

Preparation of OP-1 from Natural Sources

For a detailed description of the procedure for purifying OP-1 from bovine bone, see Oppermann et al., U.S. Pat. No. 5,324,819, which is incorporated herein by reference.

Preparation of Demineralized Bone

Demineralized bovine bone matrix is prepared using previously published procedures (Sampath and Reddi, Proc.

Natl. Acad. Sci. USA, 80, pp. 6591–95 (1983)). Fresh bovine diaphyseal bones (age 1–10 days) are stripped of muscle and fat, cleaned of periosteum, demarrowed by pressure with cold water, dipped in cold absolute ethanol, and stored at −20° C. They are then dried and fragmented by crushing and pulverized in a large mill using liquid nitrogen to prevent heating. The pulverized bone is milled to a particle size between 70–420 mm and is defatted by two washes of approximately two hours duration with three volumes of chloroform and methanol (3:1). The particulate bone is then washed with one volume of absolute ethanol and dried over one volume of anhydrous ether. Alternatively, Bovine Cortical Bone Powder (75–425 mm) may be purchased from American Biomaterials.

The defatted bone powder is demineralized with 10 volumes of 0.5 N HCl at 4° C. for 40 min., four times. Finally, neutralizing washes are done on the demineralized bone powder with a large volume of water.

Demineralized bone powder is then used as a starting material for performing the following purification steps, which are explained in detail in Oppermann et al., U.S. Pat. No. 5,324,819:

1. Dissociative extraction and ethanol precipitation;
2. Heparin-sepharose chromatography I;
3. Hydroxyapatite-ultrogel chromatography;
4. Sephacryl S-300 gel exclusion chromatography;
5. Heparin-sepharose chromatography II; and
6. Reverse phase HPLC SDS gel electrophoresis may be performed to visualize and characterize further the species separated by HPLC; gel eluted species may be filtered, concentrated and prepared further for sequencing and other desired characterizations. The yield is typically 0.5 to 1.0 μg substantially pure osteogenic protein per kg of bone.

For additional details on these procedures and the chemical characterization of the naturally-derived osteogenic proteins, see also Oppermann et al., U.S. Pat. No. 5,258,494, which is incorporated herein by reference.

EXAMPLE 2

Preparation of Recombinant Osteogenic Protein

A. Expression in E. Coli

Using recombinant DNA techniques, various fusion genes can be constructed to induce recombinant expression of naturally-sourced osteogenic sequences in a procaryotic host such as E. coli. Full-length or truncated forms of the morphogenic genes encoding OP-1 or BMP-2 were cloned into a bacterial expression vector downstream from an acid labile Asp-Pro cleavage site under the control of a synthetic trp promoter-operator. Vectors were introduced into an appropriate E. coli strain by transformation and the bacteria were grown up to produce insoluble inclusion bodies.

The inclusion bodies were solubilized in 8M urea following lysis, dialyzed against 1% acetic acid, and partly purified by differential solubilization. Constructs containing the Asp-Pro site were cleaved with acid. The resulting products were passed through a Sephacryl-200HR or SP Trisacyl column to further purify the proteins, and then subjected to HPLC on a semi-prep C-18 column to separate the leader proteins and other minor impurities from the morphogenic protein constructs.

Morphogenic proteins OP-1 and BMP-2 were purified by chromatography on heparin-Sepharose. The output of the HPLC column was lyophilized at pH 2 so that it remained reduced.

Conditions for refolding were at pH 8.0 using Tris buffer and 6M guanidine-HCl at a protein concentration of several mg/ml. Those solutions were diluted with water to produce a 2M or 3M guanidine concentration and left for 18 hours at 4° C. Air dissolved or entrained in the buffer assured oxidation of the protein in these circumstances.

Samples of the various purified constructs and various mixtures of pairs of the constructs refolded together were applied to SDS polyacrylamide gels, separated by electrophoresis, sliced, incorporated in a matrix as disclosed below, and tested for osteogenic activity.

These studies demonstrated that each of the constructs (full-length or truncated versions) have true osteogenic activity. In addition, mixed species including heterodimers were also osteogenically active and may include heterodimers. For specific combinations tested, see Oppermann et al., U.S. Pat. No. 5,354,557). Finally, single and mixed species of analogs of the active region, e.g., COP5 and COP7, disclosed in U.S. Pat. No. 5,011,691, also induce osteogenesis, as determined by histological examination.

After N-terminal sequencing of the various constructs to confirm their identity, polyclonal antisera against the recombinant presumed mature form proteins were produced. The human OP-1 antisera reacted with both the glycosylated and unglycosylated higher molecular weight subunits of naturally sourced bovine material. Antisera against recombinant mature human BMP-2 reacted with both the glycosylated and unglycosylated lower molecular weight subunit of naturally sourced bovine material. While there was some cross-reactivity, this was expected in view of the significant homology between BMP-2 and OP-1 (approx. 60% identity), and the likelihood that degraded OP-1 generated during purification contaminates the lower molecular weight subunit. Both antisera react with the naturally sourced 30 ka dimeric bOP.

In addition, synthetic osteogenic sequences produced by assembly of chemically-synthesized oligonucleotides (see above) may be expressed in appropriate prokaryotic hosts. See Oppermann et al., U.S. Pat. No. 5,324,819, which is herein incorporated by reference, for an exemplary plasmid and protocol. An expression vector based on pBR322 and containing a synthetic trp promoter, operator and the modified trp LE leader can be opened at the EcoRI and PstI restriction sites, and a FB-FB COP gene fragment can be inserted between these sites, where FB is a fragment B of Staphylococcal Protein A. The expressed fusion protein results from attachment of the COP gene to a fragment encoding FB. The COP protein is joined to the leader protein via a hinge region having the sequence asp-pro-asn-gly. This hinge permits chemical cleavage of the fusion protein with dilute acid at the asp-pro site or cleavage at asn-gly with hydroxylamine. Cleavage at the hinge releases COP protein.

2. Mammalian Cell Expression

Recombinant production of mammalian proteins for therapeutic uses may be expressed in mammalian cell culture systems in order to produce a protein whose structure is most like that of the natural material. Recombinant protein production in mammalian cells requires the establishment of appropriate cells and cell lines that are easy to transfect, are capable of stably maintaining foreign DNA with an unrearranged sequence, and which have the necessary cellular components for efficient transcription, translation, post-translation modification, and secretion of the protein. In addition, a suitable vector carrying the gene of interest is necessary.

DNA vector design for transfection into mammalian cells should include appropriate sequences to promote expression of the gene of interest, including appropriate transcription initiation, termination, and enhancer sequences, as well as sequences that enhance translation efficiency, such as the Kozak consensus sequence. Preferred DNA vectors also include a marker gene and means for amplifying the copy number of the gene of interest.

Substantial progress in the development of mammalian cell expression systems has been made in the last decade and many aspects of the system are well characterized. A detailed review of the state of the art of the production of foreign proteins in mammalian cells, including useful cells, protein expression-promoting sequences, marker genes, and gene amplification methods, is disclosed in Bendig, Mary M., *Genetic Engineering*, 7, pp. 91–127 (1988).

Briefly, among the best characterized transcription promoters useful for expressing a foreign gene in a particular mammalian cell are the SV40 early promoter, the adenovirus promoter (AdMLP), the mouse metallothionein-I promoter (mMT-I), the Rous sarcoma virus (RSV) long terminal repeat (LTR), the mouse mammary tumor virus long terminal repeat (MMTV-LTR), and the human cytomegalovirus major intermediate-early promoter (hCMV). The DNA sequences for all of these promoters are known in the art and are available commercially.

One of the better characterized methods of gene amplification in mammalian cell systems is the use of the selectable dihydrofolate reductase (DHFR) gene in a dhfr-cell line. Generally, the DHFR gene is provided on the vector carrying the gene of interest, and addition of increasing concentrations of the cytotoxic drug methotrexate leads to amplification of the DHFR gene copy number, as well as that of the associated gene of interest. DHFR as a selectable, amplifiable marker gene in transfected chinese hamster ovary cell lines (CHO cells) is particularly well characterized in the art. Other useful amplifiable marker genes include the adenosine deaminase (ADA) and glutamine synthetase (GS) genes.

In the currently preferred expression system, gene amplification is further enhanced by modifying marker gene expression regulatory sequences (e.g., enhancer, promoter, and transcription or translation initiation sequences) to reduce the levels of marker protein produced. Lowering the level of DHFR transcription has the effect of increasing the DHFR gene copy number (and the associated OP-1 gene) in order for a transfected cell to adapt to grow in even low levels of methotrexate (MTX) (e.g., 0.1 $\mu$M MTX). Preferred expression vectors (pH754 and pH752), have been manipulated using standard recombinant DNA technology, to create a weak DHFR promoter. As will be appreciated by those skilled in the art, other useful weak promoters, different from those disclosed and preferred herein, can be constructed using standard vector construction methodologies. In addition, other, different regulatory sequences also can be modified to achieve the same effect.

The choice of cells/cell lines is also important and depends on the needs of the experimenter. Monkey kidney cells (COS) provide high levels of transient gene expression, providing a useful means for rapidly testing vector construction and the expression of cloned genes. COS cells are transfected with a simian virus 40 (SV40) vector carrying the gene of interest. The transfected COS cells eventually die, thus preventing the long term production of the desired protein product. However, transient expression does not require the time consuming process required for the development of a stable cell line.

Among established cell lines, CHO cells may be the best characterized to date, and are the currently preferred cell line for mammalian cell expression of recombinant osteogenic protein. CHO cells are capable of expressing proteins from a broad range of cell types. The general applicability of CHO cells and its successful production for a wide variety of human proteins in unrelated cell types emphasizes the underlying similarity of all mammalian cells. Thus, while the glycosylation pattern on a recombinant protein produced in a mammalian cell expression system may not be identical to the natural protein, the differences in oligosaccharide side chains are often not essential for biological activity of the expressed protein.

The methodology disclosed herein includes the use of COS cells for the rapid evaluation of vector construction and gene expression, and the use of established cell lines for long term protein production. Of the cell lines disclosed, OP-1 expression from CHO cell lines currently is most preferred.

Several different mammalian cell expression systems have been used to express recombinant OP-1 proteins which may be used in concert with a MPSF according to this invention. In particular, COS cells are used for the rapid assessment of vector construction and gene expression, using an SV40 vector to transfect the DNA sequence into COS cells. Stable cell lines are developed using CHO cells (chinese hamster ovary cells) and a temperature-sensitive strain of BSC cells (simian kidney cells, BSC40-tsA58; *Biotechnology*, 6, pp. 1192–96 (1988)) for the long term production of OP-1.

Two different promoters were found most useful to transcribe hOP1 (Seq. ID No. 1): the CMV promoter and the MMTV promoter, boosted by the enhancer sequence from the Rous sarcoma virus LTR. The mMT promoter (mouse metallothionein promoter) and the SV40 late promoter have also been tested. Several selection marker genes also are used, namely, neo (neomycin) and DHFR.

The DHFR gene also may be used as part of a gene amplification scheme for CHO cells. Another gene amplification scheme relies on the temperature sensitivity (ts) of BSC40-tsA58 cells transfected with an SV40 vector. Temperature reduction to 33° C. stabilizes the ts SV40 T antigen which leads to the excision and amplification of the integrated transfected vector DNA, thereby also amplifying the associated gene of interest.

Stable cell lines were established for CHO cells as well as BSC40-tsA58 cells (hereinafter referred to as "BSC cells"). The various cells, cell lines and DNA sequences chosen for mammalian cell expression of the OP-1 proteins of this invention are well characterized in the art and are readily available. Other promoters, selectable markers, gene amplification methods and cells also may be used to express the OP-1 proteins of this invention, as well as other osteogenic proteins. Particular details of the transfection, expression, and purification of recombinant proteins are well documented in the art and are understood by those having ordinary skill in the art. Further details on the various technical aspects of each of the steps used in recombinant production of foreign genes in mammalian cell expression systems can be found in a number of texts and laboratory manuals in the art. See, e.g., F. M. Ausubel et al., ed., *Current Protocols in Molecular Biology*, John Wiley & Sons, New York (1989).

a) Exemplary Expression Vectors

Restriction maps and sources of various exemplary expression vectors designed for OP-1 expression in mammalian cells have been described (Oppermann et al., U.S. Pat. No. 5,354,557, incorporated herein by reference; see FIGS. 19 (A–F) and accompanying text). Each of these vector constructs employs a full-length cDNA sequence ("hOP1"; Seq. ID No. 1) originally isolated from a human cDNA library (placenta) and subsequently cloned into a conventional pUC vector (pUC-18) using pUC polylinker sequences at the insertion sites.

It will be appreciated by those skilled in the art that DNA sequences encoding truncated forms of osteogenic protein may also be used in these vectors, provided that the expression vector or host cell then provides the sequences necessary to direct processing and secretion of the expressed protein.

Each vector employs an SV40 origin of replication (ori), useful for mediating plasmid replication in primate cells (e.g., COS and BSC cells). In addition, the early SV40 promoter is used to drive transcription of marker genes on the vector (e.g., neo and DHFR).

The pH717 expression vector (FIG. 19A) contains the neomycin (neo) gene as a selection marker. This marker gene is well characterized in the art and is available commercially. Alternatively, other selectable markers may be used. The particular vector used to provide the neo gene DNA fragment for pH717 may be obtained from Clontech, Inc., Palo Alto, Calif. (pMAM-neo-blue). This vector also may be used as the backbone. In pH717, hOP1 transcription is driven by the CMV promoter with RSV-LTR (Rous sarcoma virus long terminal repeat) and MMTV-LTR (mouse mammary tumor virus long terminal repeat) enhancer sequences. These sequences are known in the art, and are available commercially. For example, vectors containing the CMV promoter sequence (e.g., pCDM8) may be obtained from Invitrogen Inc., San Diego, Calif.

Expression vector pH731 (FIG. 19B), utilizes the SV40 late promoter to drive hOP1 transcription. As indicated above, the sequence and characteristics of this promoter also are well known in the art. For example, pH731 may be generated by inserting the SmaI-BamHI fragment of hOP1 into pEUK-C1 (Clontech, Inc., Palo Alto, Calif.).

The pH752 and pH754 expression vectors contain the DHFR gene under SV40 early promoter control, as both a selection marker and as an inducible gene amplifier. The DNA sequence for DHFR is well characterized in the art, and is available commercially. For example, pH754 may be generated from pMAM-neo (Clontech, Inc., Palo Alto, Calif.) by replacing the neo gene (BamHI digest) with an SphI-BamHI, or a PvuII-BamHI fragment from pSV5-DHFR (ATCC #37148), which contains the DHFR gene under SV40 early promoter control. A BamHI site can be engineered at the SphI or PvuII site using standard techniques (e.g., by linker insertion or site-directed mutagenesis) to allow insertion of the fragment into the vector backbone. hOP1 DNA can be inserted into the polylinker site downstream from the MMTV-LTR sequence, yielding pH752 (FIG. 19D). The CMV promoter sequence then may be inserted into pH752 (e.g., from pCDM8, Invitrogen, Inc.), yielding pH754 (FIG. 19C).

The SV40 early promoter, which drives DHFR expression, is modified in these vectors to reduce the level of DHFR mRNA produced. Specifically, the enhancer sequences and part of the promoter sequence have been deleted, leaving only about 200 bases of the promoter sequence upstream of the DHFR gene. Host cells transfected with these vectors are adapted to grow in 0.1 $\mu$M MTX and can increase OP-1 production significantly (see, e.g., Table 8, Oppermann et al., U.S. Pat. No. 5,354,557).

The pW24 vector (FIG. 19E), is essentially identical in sequence to p754, except that neo is used as the marker gene (see pH717)in place of DHFR. Similarly, pH783 (FIG. 19F) contains the amplifiable marker DHFR, but here OP-1 is under mMT (mouse metallothionein promoter) control. The mMT promoter is well characterized in the art and is available commercially.

All vectors tested are stable in the various cells used to express OP-1, and provide a range of OP-1 expression levels.

b) Exemplary Mammalian Cells

Recombinant OP-1 has been expressed in three different cell expression systems: COS cells for rapidly screening the functionality of the various expression vector constructs, CHO cells for the establishment of stable cell lines, and BSC40-tsA58 cells as an alternative means of producing OP-1 protein. The CHO cell expression system disclosed herein is contemplated to be the best mode currently known for long-term recombinant OP-1 production in mammalian cells.

(1) COS Cells

COS cells (simian kidney cells) are used for rapid screening of vector constructs and for immediate, small scale production of OP-1 protein. COS cells are well known in the art and are available commercially. The particular cell line described herein may be obtained through the American Type Culture Collection (ATCC #COS-1, CRL-1650).

OP-1 expression levels from these different expression vectors, analyzed by Northern and Western blot assays, are compared Oppermann et al. (see Table 7, Oppermann et al.).

Large scale preparations of OP-1 from transfected COS cells may be produced using conventional roller bottle technology. Briefly, $14 \times 10^6$ cells are used to seed each bottle. After 24 hrs of growth, the cells are transfected with 10 $\mu$g of vector DNA (e.g., pH717) per $10^6$ cells, using the DEAE-dextran method. Cells are then conditioned in serum-free media for 120 hr before harvesting the media for protein analysis. Following this protocol, OP-1 yield is approximately 2–6 ng/ml.

(2) BSC CELLS

The BSC40-tsA58 cell line ("BSC cells") is a temperature-sensitive (ts) strain of simian kidney cells (Biotechnology, 6, pp. 1192–96 (1988)) which overcomes some of the problems associated with COS cells. These BSC cells have the advantage of being able to amplify gene sequences rapidly on a large scale with temperature downshift, without requiring the addition of exogenous, potentially toxic drugs. In addition, after induction and stimulation of OP-1 expression, the cells may be transferred to new growth medium, grown to confluence at 39.5° C. and induced a second time by downshifting the temperature to 33° C. BSC cells may be used to establish stable cell lines rapidly for protein production.

OP-1 expression in transfected BSC cells may be induced by shifting the temperature down to 33° C. in media containing 10% FCS, and harvesting the conditioned media after 96 hrs of incubation. Comparable amounts of OP-1 mRNA and protein are obtained, as compared with CHO cells (e.g., 100–150 ng OP-1/ml conditioned media from BSC clones transfected with pH717, see Oppermann et al.).

(3) CHO Cells

CHO cells (chinese hamster ovary cells) may be used for long term OP-1 production and are the currently preferred cell line for mammalian cell expression of OP-1. CHO cell lines are well characterized for the small and large scale production of foreign genes and are available commercially. See Oppermann et al., U.S. Pat. No. 5,354,557, incorporated herein by reference, for a detailed description of: establishing a stable transfected cell line with high hOP-1 expression levels, subcloning transfected cells to obtain high expression subclones, characterizing subclone DNA insert copy numbers, and screening subclones for OP-1 mRNA and protein expression levels. Oppermann et al. also provides a detailed description of a rapid purification method for obtaining recombinantly produced OP-1 of about 90% purity, and further data demonstrating the physical characteristics (molecular weight and glycosylation profiles) and osteogenic activities of a variety of recombinant forms of OP-1 expressed in the cell lines described above.

Accordingly, it is anticipated that active mature OP-1 sequences, including full-length, truncated and mutationally-altered active forms of the protein, can be expressed from other different prokaryotic and eukaryotic cell expression systems using procedures essentially as described herein. The proteins produced may have varying N-termini, and those expressed from eukaryotic cells may have varying glycosylation patterns. Finally, it will also be appreciated that these variations in the recombinant osteogenic protein produced will be characteristic of the host cell expression system used rather than of the protein itself.

EXAMPLE 3
Synergistic Effect of Exogenous IGF-I on the OP-1-induced Differentiation of Fetal Rat Calvarial (FRC) Cells Primary osteoblast cell cultures were prepared from fetal rat calvaria using published procedures (M. A. Aronow et al., *J. Cell Physiol.*, 143, pp. 213–221 (1990); T. K. McCarthy et al., *J. Bone Miner. Res.*, 3, pp. 401–8 (1988)). Briefly, cells were harvested by sequential collagenase digestions of the calvarium and cells from digestions III to V were pooled. Fetal rat calvaria (FRC) cells were plated in complete medium (MEM, alpha; GIBCO/BRL, Grand Island, N.Y.) containing 10% fetal bovine serum, vitamin C (100 $\mu$g/ml), and antibiotics (100 U/ml penicillin, and 100 mg/ml streptomycin). Cultures were incubated at 37° C. with 95% air/5% $CO_2$ for several days to reach confluence. Cells were then subcultured for experimentations.

FRC cells were subcultured in 48-well plates (COSTAR, Cambridge, Mass.) in complete MEM medium with 10% fetal bovine serum until confluent in about 4 days. Confluent cells were rinsed with Hank's balanced salt solution (HBSS) and treated with serum-free α-MEM medium (with 0.1% BSA, 100 U/ml penicillin, and 100 mg/ml streptomycin) containing the appropriate solvent vehicle (50% acetonitrile/0.1% trifluoroacetic acid for OP-1 treatment or 0.1N acetic acid for IGFI treatment) or recombinant human OP-1, or IGFI at the concentrations indicated. Solvent vehicle concentration in the culture medium never exceeded 0.1%. At the end of treatment, cells were lysed and total cellular alkaline phosphatase activity was measured (typically after 48 hours of treatment).

Confluent FRC cells (6–8×10$^6$ cells/T-150 flask) were rinsed once with HBSS to remove the complete medium and then incubated in serum-free α-MEM medium (with 0.1% BSA, 100 U/ml penicillin, and 100 mg/ml streptomycin) in the presence or absence of OP-1 for varying intervals. OP-1 was dissolved in 50% acetonitrile and 0.1% trifluoroacetic acid (TFA). At the end of treatments, cells in the T-150 flask were rinsed with ice-cold PBS solution to remove serum-free medium and used for subsequent RNA isolation.

Alkaline phosphatase Activity Assay

Total cellular alkaline phosphatase activity was determined using a commercial assay kit (Sigma, St. Louis, Mo.). Cell lysates were prepared by aspirating the medium from the 48-well plate, rinsing the cells with ice-cold PBS, and lysing the cells with 0.05% Triton X-100 and sonication for 60 sec. Alkaline phosphatase activity in the lysates was measured in 2-amino-2-methyl-1-propanol buffer (pH 10.3) with p-nitrophenyl phosphate as substrate at 37° C. Reactions were performed in 96-well plates for 1–2 h. Following color development, reactions were terminated with 0.5N NaOH. Absorbance of the reaction was measured at 405 nm using a Hewlett Packard Genenchem automatic plate reader. Total protein level in the lysates was measured according to Bradford (M. Bradford, *Anal. Biochem.*, 72, pp.248–54 (1976)) using bovine serum albumin as a standard. Alkaline phosphatase activity was expressed as nmol p-nitrophenol liberated per microgram of total cellular protein.

RNA isolation

Total RNA was isolated with cold Utraspec (Biotecx Lab., Houston, Tex.) following the manufacturer's recommendation. RNA was recovered by precipitation and dissolved in DEPC-$H_2O$. The amount of RNA recovered was estimated by $A_{260}$ reading. The integrity of the RNA preparation was examined by gel electrophoresis on 1% agarose. RNA was detected by EtBr staining. Only RNA preparations showing intact species were used for subsequent analyses.

Northern blot analysis

Total RNAs (20 $\mu$g) were denatured with formaldehyde and formamide at 65° C. for 15 min and analyzed on a 1% GTG agarose gel containing 2.2 M formaldehyde. RNA standards (0.24–9.5 kb) from GIBCO/BRL (Grand Island, N.Y.) were used as size markers. The fractionated RNA was transferred onto 'Nytran plus" membrane using a Turboblot apparatus (Schleicher & Schuell, Inc., Keene, N.H.). The lane containing the standards was cut from the blot and stained with methylene blue. The RNA was covalently linked to the membrane using a UV Crosslinker (Stratagene, La Jolla, Calif.). The membranes were hybridized overnight at 42° C. with the osteocalcin or type I collagen DNA probes, washed twice in 2×SSC at room temperature for 20 min each, twice in 2×SSC/1% SDS at 60° C. for 1 hour each, and finally twice in 0.1×SSC at room temperature for 30 min each. The blots were exposed to a PhosphorImage screen and analyzed as described above. Four blots with different RNA preparations were repeated for each probe.

Statistical Analysis

Multiple means were compared with one-way analysis of variance, followed by the student t-test for paired comparisons with the control, using the ANOVA and T-Test programs in PSIPlot (Poly Software International, Salt Lake City, Utah) for personal computers.

EXAMPLE 4

Identifying a First MPSF that Stimulates Tissue Induction by a Morphogenic Protein The FRC cell alkaline phosphatase (AP) assay was performed as described in Example 3 to test increasing concentrations of putative MPSFs in combination with a single concentration (200 ng/ml) of osteogenic protein OP-1.

At least four experimental groups were tested: control cells treated with no OP-1 or MPSF; group I cells treated with increasing concentrations of MPSF alone; group II cells treated with 200 ng/ml of OP-1 alone; and group III cells, treated with 200 ng/ml OP-1 in the presence of increasing concentrations of the MPSF.

Figure 5:
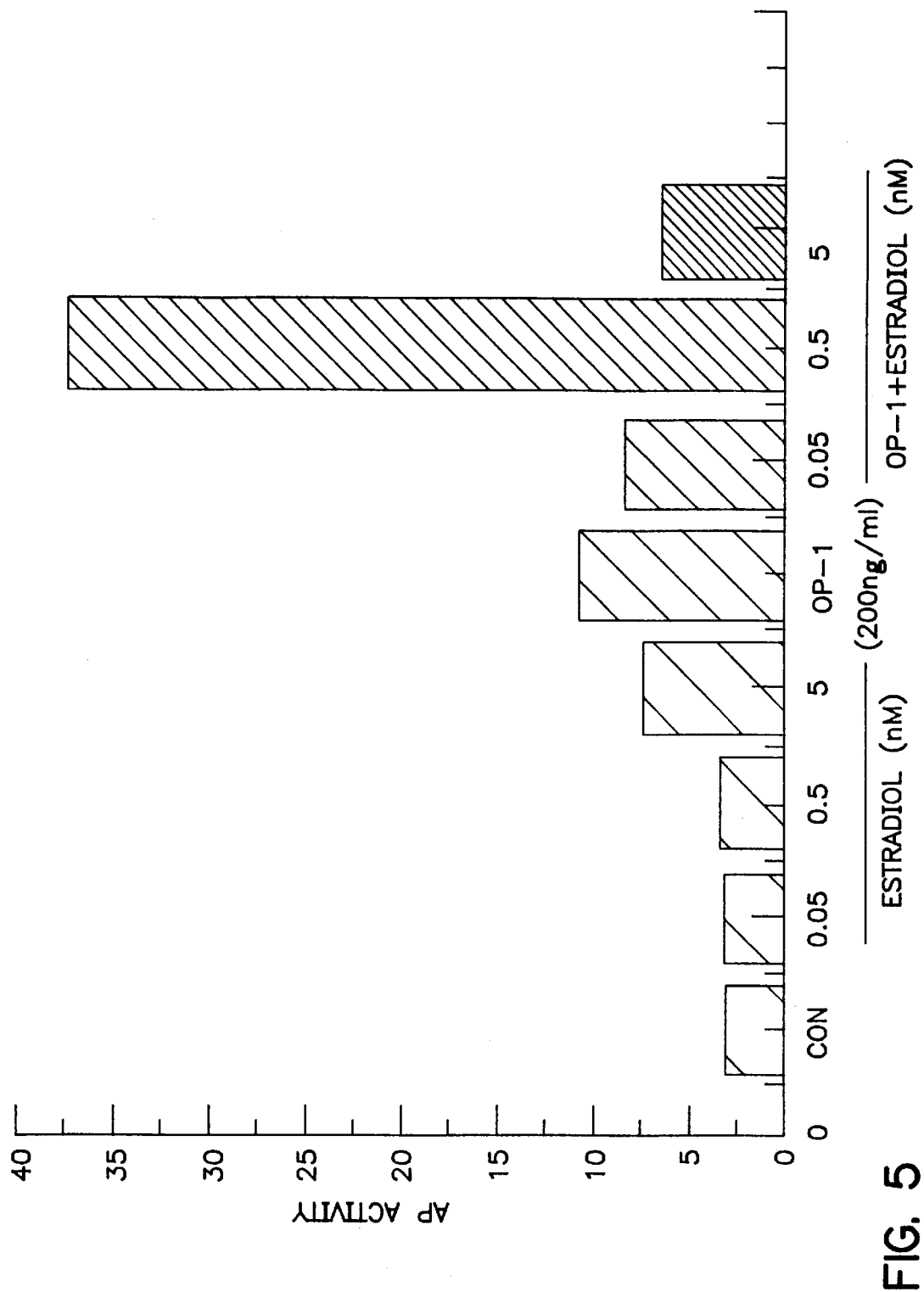
FIG. 5. Estradiol is a MPSF in concert with OP-1. Alkaline phosphatase (AP) activity (nmol/$\mu$g protein) in FRC cells is indicated. FRC cells were grown in serum free media containing OP-1 alone (200 ng/ml), or containing increasing concentrations of estradiol (0.05, 0.5 and 5.0 nM) in the presence or absence of 200 ng/ml OP-1. Control cultures (CON) were grown in serum free media containing solvent vehicles.

FIG. 5 shows the effects of estradiol (0.05–5.0 nM; purchased from Sigma, St. Louis, Mo.) and 200 ng/ml of OP-1 on FRC cell alkaline phosphatase activity at 48 hours post-treatment. Estradiol alone did not appear to stimulate AP activity. In the presence of 0.5 nM estradiol and 200 ng/ml of OP-1, the level of AP activity was almost eleven-fold higher than the control, and about three-fold higher than cells treated with OP-1 alone.

FIG. 6 shows the effects of growth hormone (hGH; 10–1000 ng/ml; purchased from Sigma, St. Louis, Mo.) and 200 ng/ml of OP-1 on FRC cell alkaline phosphatase activity after 48 hours. All concentrations of hGH tested in the presence of 200 ng/ml of OP-1 stimulated the induction of AP activity over that observed for OP-1 alone ("0"). Higher hGH concentrations appeared to have more of a stimulatory effect than lower concentrations.

FIG. 7 shows the effects of hydrocortisone (HC; 0.05–5 nM; purchased from Sigma, St. Louis, Mo.) and 200 ng/ml of OP-1 on FRC cell alkaline phosphatase activity after 48 hours. HC alone did not stimulate AP activity in FRC cells. In the presence of 0.5 nM HC and 200 ng/ml OP-1, the level of AP activity is about three-fold higher than in control cells, and about two-fold higher than in cells treated with OP-1 alone.

Figure 8:
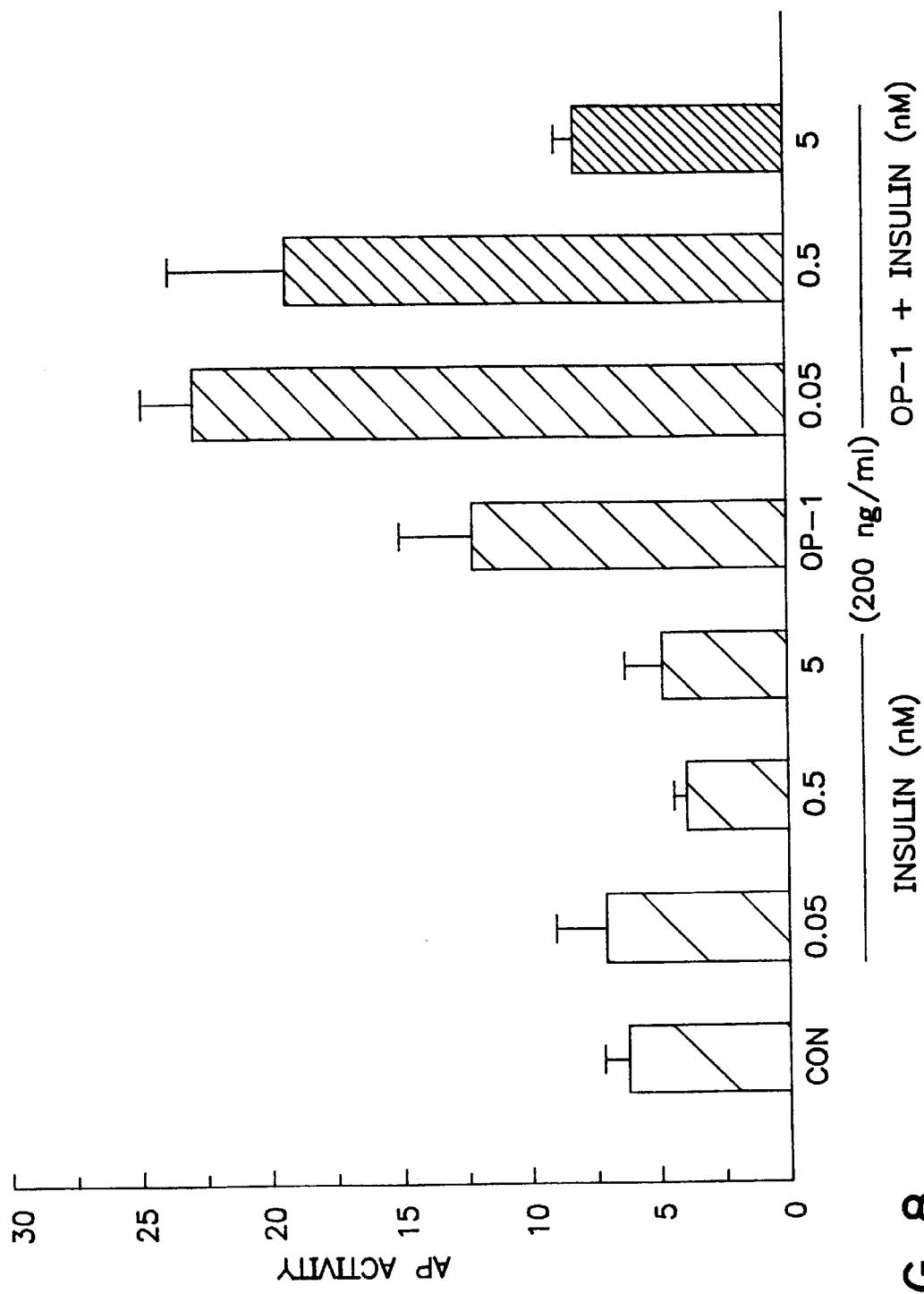
FIG. 8. Insulin is a MPSF in concert with OP-1. Alkaline phosphatase (AP) activity (nmol/$\mu$g protein) in FRC cells is indicated. FRC cells were incubated in serum free media containing OP-1 alone (200 ng/ml), or containing increasing concentrations of insulin (0.05, 0.5 and 5.0 nM) in the presence or absence of 200 ng/ml OP-1. Control cultures (CON) were grown in serum free media containing solvent vehicles.

FIG. 8 shows the effects of insulin (0.05–5 nM; purchased from Sigma, St. Louis, Mo.) and 200 ng/ml of OP-1 on FRC cell alkaline phosphatase activity after 48 hours. Insulin alone did not stimulate AP activity in FRC cells. In the presence of 0.05 nM or 0.5 nM insulin and 200 ng/ml OP-1, the level of AP activity is about four-fold higher than in control cells, and about two-fold higher than in cells treated with OP-1 alone.

FIG. 9 shows the effects of parathyroid hormone (PTH; 25–200 nM; purchased from Sigma, St. Louis, Mo.) and 200 ng/ml of OP-1 on FRC cell alkaline phosphatase activity after 48 hours. PTH alone did not stimulate AP activity in FRC cells. Low concentrations of PTH (25 and 100 nM) and 200 ng/ml OP-1 appear to have no effect on OP-1-induced stimulation of AP activity. In the presence of 200 nM PTH and 200 ng/ml OP-1, the level of AP activity is about five-fold higher than in control cells, and about two-fold higher than in cells treated with OP-1 alone.

Finally, FIG. 10 shows the effects of progesterone (PG; 0.05–5 nM; purchased from Sigma, St. Louis, Mo.) and 200 ng/ml of OP-1 on FRC cell alkaline phosphatase activity after 48 hours. PG alone (5 nM) appears to stimulate AP activity about three-fold beyond control cells. PG (5 nM) in the presence of 200 ng/ml OP-1 appear to increase the level of AP activity about four-fold higher than in control cells, and about two-fold higher than in cells treated with OP-1 alone.

EXAMPLE 5

Identifying Additional MPSFs that Stimulate Tissue Induction by a Morphogenic Protein/MPSF Combination Once an effective morphogenic protein/MPSF combination has been identified, one or more additional MPSFs that increase further the stimulation of tissue induction by that morphogenic protein/MPSF combination may be identified. An assay done essentially according to the procedures set forth in Examples 3 and 4 was performed except that FRC cells were incubated with a combination of 200 ng/ml of OP-1 and 25 ng/ml of IGF-1 in the presence or absence of increasing concentrations of PTH (25–200 nM). The presence of PTH (at concentrations of at least about 50 nM) significantly increased the AP activity induced by the OP-1/IGF-I combination.

EXAMPLE 6

Preparation of Bone-Derived Matrices for Use in Morphogenic Devices

Demineralized bone matrix, preferably bovine bone matrix, is prepared using previously published procedures (Sampath and Reddi, *Proc. Natl. Acad. Sci. USA,* 80, pp. 6591–95 (1983)), as described in Example 1.

Demineralized bone matrix is extracted with 5 volumes of 4M guanidine-HCl, 50 mM Tris-HCl, pH 7.0 for 16 hr. at 4° C. The suspension is filtered. The insoluble material is collected and used to fabricate the matrix. The material is mostly collagenous in nature and is devoid of osteogenic or chondrogenic activity.

The major component of all bone matrices is Type-I collagen. In addition to collagen, demineralized bone extracted includes non-collagenous proteins which may account for 5% of its mass. In a xenogenic matrix, these non-collagenous components may present themselves as potent antigens, and may constitute immunogenic and/or inhibitory components. These components also may inhibit osteogenesis in allogenic implants by interfering with the developmental cascade of bone differentiation.

Treatment of the matrix particles with a collagen fibril-modifying agent extracts potentially unwanted components from the matrix, and alters the surface structure of the matrix material. Useful agents include acids, organic solvents or heated aqueous media. Various treatments are described below. A detailed physical analysis of the effect these fibril-modifying agents have on demineralized, quanidine-extracted bone collagen particles is disclosed in U.S. Pat. No. 5,171,574, the disclosure of which is hereby incorporated by reference.

After contact with the fibril-modifying agent, the treated matrix is washed to remove any extracted components, following a form of the procedure set forth below:

1. Suspend in TBS (Tris-buffered saline) 1 g/200 ml and stir at 4° C. for 2 hrs; or in 6M urea, 50 mM Tris-HCl, 500 mM NaCl, pH 7.0 (UTBS) or water and stir at room temperature (RT) for 30 minutes (sufficient time to neutralize the pH);

2. Centrifuge and repeat wash step; and

3. Centrifuge; discard supernatant; wash residue with water; and lyophilize.

Acid Treatments

1. TRIFLUOROACETIC ACID

Trifluoroacetic acid is a strong non-oxidizing acid that is a known swelling agent for proteins, and which modifies collagen fibrils.

Bovine bone residue prepared as described above is sieved, and particles of the appropriate size are collected. These particles are extracted with various percentages (1.0% to 100%) of trifluoroacetic acid and water (v/v) at 0° C. or at room temperature for 1–2 hours with constant stirring. The treated matrix is filtered, lyophilized, or washed with water/salt and then lyophilized.

2. HYDROGEN FLUORIDE

Like trifluoroacetic acid, hydrogen fluoride (HF) is a strong acid and swelling agent, and also is capable of altering intraparticle surface structure. Hydrogen fluoride is also a known deglycosylating agent. As such, HF may function to increase the osteogenic activity of these matrices by removing the antigenic carbohydrate content of any glycoproteins still associated with the matrix after guanidine extraction.

Bovine bone residue prepared as described above is sieved, and particles of the appropriate size are collected. The sample is dried in vacuo over P2O5, transferred to the reaction vessel and exposed to anhydrous hydrogen fluoride (10–20 ml/g of matrix) by distillation onto the sample at −70° C. The vessel is allowed to warm to 0° C. and the reaction mixture is stirred at this temperature for two hours.

After evaporation of the hydrogen fluoride in vacuo, the residue is dried thoroughly in vacuo over KOH pellets to remove any remaining traces of acid. Extent of deglycosylation can be determined from carbohydrate analysis of matrix samples taken before and after treatment with hydrogen fluoride, after washing the samples appropriately to remove non-covalently bound carbohydrates. SDS-extracted protein from HF-treated material is negative for carbohydrate as determined by Con A blotting.

The deglycosylated bone matrix is next washed twice in TBS (Tris-buffered saline) or UTBS, water-washed, and then lyophilized.

Other acid treatments are envisioned in addition to HF and TFA. TFA is a currently preferred acidifying reagent in these treatments because of its volatility. However, it is understood that other, potentially less caustic acids may be used, such as acetic or formic acid.

Solvent Treatments

1. DICHLOROMETHANE

Dichloromethane (DCM) is an organic solvent capable of denaturing proteins without affecting their primary structure. This swelling agent is a common reagent in automated peptide synthesis, and is used in washing steps to remove components. Bovine bone residue, prepared as described above, is sieved, and particles of the appropriate size are incubated in 100% DCM or, preferably, 99.9% DCM/0.1% TFA. The matrix is incubated with the swelling agent for one or two hours at 0° C. or at room temperature. Alternatively, the matrix is treated with the agent at least three times with short washes (20 minutes each) with no incubation.

2. ACETONITRILE

Acetonitrile (ACN) is an organic solvent capable of denaturing proteins without affecting their primary structure. It is a common reagent used in high-performance liquid chromatography, and is used to elute proteins from silica-based columns by perturbing hydrophobic interactions.

Bovine bone residue particles of the appropriate size, prepared as described above, are treated with 100% ACN (1.0 g/30 ml) or, preferably, 99.9% ACN/0.1% TFA at room temperature for 1–2 hours with constant stirring. The treated matrix is then water-washed, or washed with urea buffer or 4M NaCl, and lyophilized. Alternatively, the ACN or ACN/TFA treated matrix may be lyophilized without wash.

3. ISOPROPANOL

Isopropanol is also an organic solvent capable of denaturing proteins without affecting their primary structure. It is a common reagent used to elute proteins from silica HPLC columns. Bovine bone residue particles of the appropriate size prepared as described above are treated with 100% isopropanol (1.0 g/30 ml) or, preferably, in the presence of 0.1% TFA, at room temperature for 1–2 hours with constant stirring. The matrix is then water-washed or washed with urea buffer or 4M NaCl before being lyophilized.

4. CHLOROFORM

Chloroform also may be used to increase surface area of bone matrix like the reagents set forth above, either alone or acidified. Treatment as described above is effective to assure that the material is free of pathogens prior to implantation.

Heat Treatment

The currently most preferred agent is a heated aqueous fibril-modifying medium such as water, to increase the matrix particle surface area and porosity. The currently most preferred aqueous medium is an acidic aqueous medium having a pH of less than about 4.5, e.g., within the range of about pH 2–pH 4 which may help to "swell" the collagen before heating. Acetic acid (0.1%), which has a pH of about 3, currently is most preferred. 0.1M acetic acid also may be used.

Various amounts of delipidated, demineralized guanidine-extracted bone collagen are heated in the aqueous medium (1 g matrix/30 ml aqueous medium) under constant stirring in a water jacketed glass flask, and maintained at a given temperature for a predetermined period of time. Preferred treatment times are about one hour, although exposure times of between about 0.5 to two hours appear acceptable. The temperature employed is held constant at a temperature within the range of about 37° C. to 65° C. The currently preferred heat treatment temperature is within the range of about 45° C. to 60° C.

After the heat treatment, the matrix is filtered, washed, lyophilized and used for implantation. Where an acidic aqueous medium is used, the matrix also is preferably neutralized prior to washing and lyophilization. A currently preferred neutralization buffer is a 200 mM sodium phosphate buffer, pH 7.0. To neutralize the matrix, the matrix preferably is first allowed to cool following thermal treatment, the acidic aqueous medium (e.g., 0.1% acetic acid) is then removed and replaced with the neutralization buffer and the matrix agitated for about 30 minutes. The neutralization buffer may then be removed and the matrix washed and lyophilized (see infra).

The effects of heat treatment on morphology of the matrix material is described in Oppermann, et. al., U.S. Pat. No. 5,354,557. Hot aqueous treatment can increase the degree of micropitting on the particle surface (e.g., about 10-fold,) as well as also substantially increasing the particle's porosity. This alteration of the matrix particle's morphology substantially increases the particle surface area. Careful measurement of the pore and micropit sizes reveals that hot aqueous medium treatment of the matrix particles yields particle pore and micropit diameters within the range of 1 $\mu$m to 100 $\mu$m.

Oppermann et al. also show that a complete solvent extract from hot water-treated matrix inhibits OP-1 induced new bone formation in a dose dependent manner. Thus such treatment may also be removing component(s) whose association with the matrix may interfere with new bone formation in vivo.

The matrix also may be treated to remove contaminating heavy metals, such as by exposing the matrix to a metal ion chelator. For example, following thermal treatment with 0.1% acetic acid, the matrix may be neutralized in a neutralization buffer containing sodium EDTA, e.g., 200 mM sodium phosphate, 5 mM EDTA, pH 7.0. The use of 5 mM EDTA provides about a 100-fold molar excess of chelator to residual heavy metals present in the most contaminated matrix tested to date. Subsequent washing of the matrix following neutralization appears to remove the bulk of the EDTA. EDTA treatment of matrix particles reduces the residual heavy metal content of all metals tested (Sb, As, Be, Cd, Cr, Cu, Co, Pb, Hg, Ni, Se, Ag, Zn, Tl) to less than about 1 ppm. Bioassays with EDTA-treated matrices indicate that treatment with the metal ion chelator does not inhibit bone inducing activity.

The collagen matrix materials preferably take the form of a fine powder, insoluble in water, comprising nonadherent particles. It may be used simply by packing into the volume where new bone growth or sustained release is desired, held in place by surrounding tissue. Alternatively, the powder may be encapsulated in, e.g., a gelatin or polylactic acid coating, which is absorbed readily by the body. The powder may be shaped to a volume of given dimensions and held in that shape by interadhering the particles using, for example, soluble, species-biocompatible collagen. The material may also be produced in sheet, rod, bead, or other macroscopic shapes.

Demineralized rat bone matrix used as an allogenic matrix may be prepared from several of the dehydrated diaphyseal shafts of rat femur and tibia (as described in Oppermann et al., U.S. Pat. No. 5,354,557, which is incorporated herein by reference) to produce a bone particle size that passes through a 420 μm sieve. The bone particles are subjected to dissociative extraction with 4M guanidine-HCl. Such treatment results in a complete loss of the inherent ability of the bone matrix to induce endochondral bone differentiation. The remaining insoluble material is used to fabricate the matrix. The material is mostly collagenous in nature, and upon implantation, does not induce cartilage and bone formation. All new preparations are tested for mineral content and osteogenic activity before use. The total loss of biological activity of bone matrix is restored when an active morphogenic protein fraction or a substantially pure morphogenic protein preparation is reconstituted with the biologically inactive insoluble collagenous matrix.

ETHANOL TRIFLUOROACETIC ACID LYOPHILIZATION

In this procedure, morphogenic protein is solubilized in an ethanol-trifluoroacetic acid solution (47.5% EtOH/0.01% TFA) and added to the carrier material with the MPSF. Samples are vortexed and then lyophilized. This method is currently preferred.

ACETONITRILE TRIFLUOROACETIC ACID LYOPHILIZATION

This is a variation of the above procedure, using an acetonitrile-trifluoroacetic acid (ACN/TFA) solution to solubilize the morphogenic protein that is then added to the MPSF and the carrier material. Samples are vigorously vortexed many times and then lyophilized.

ETHANOL PRECIPITATION

Matrix is added to morphogenic protein and MPSF dissolved in guanidine-HCl. Samples are vortexed and incubated at a low temperature (e.g., 4° C.). Samples are then further vortexed. Cold absolute ethanol (5 volumes) is added to the mixture which is then stirred and incubated, preferably for 30 minutes at −20° C. After centrifugation (microfuge, high speed), the supernatant is discarded. The reconstituted matrix is washed twice with cold concentrated ethanol in water (85% EtOH) and then lyophilized.

UREA LYOPHILIZATION

For those morphogenic proteins that are prepared in urea buffer, the protein is mixed with the MPSF and the matrix material, gently vortexed and then lyophilized. The lyophilized material may be used "as is" for implants.

BUFFERED SALINE LYOPHILIZATION

Morphogenic protein preparations in physiological saline may also be vortexed with the MPSF and the matrix and lyophilized to produce morphogenically active material.

These procedures also can be used to adsorb other active therapeutic drugs, hormones, and various bioactive species to the matrix for sustained release purposes.

EXAMPLE 7

Rat Model Bioassay for Bone Induction

This assay consists of implanting allogenic or xenogenic test samples in subcutaneous sites in recipient rats under ether anesthesia. Male Long-Evans rats, aged 28–32 days, may be used. A vertical incision (1 cm) is made under sterile conditions in the skin over the thoracic region, and a pocket is prepared by blunt dissection. Approximately 25 mg of the test sample is implanted deep into the pocket and the incision is closed with a metallic skin clip. The day of implantation is designated as day one of the experiment. Implants are removed on day 12. The heterotropic site allows for the study of bone induction without the possible ambiguities resulting from the use of orthotropic sites.

Bone inducing activity is determined biochemically by the specific activity of alkaline phosphatase and calcium content of the day 12 implant. An increase in the specific activity of alkaline phosphatase indicates the onset of bone formation. Calcium content, on the other hand, is proportional to the amount of bone formed in the implant. Bone formation therefore is calculated by determining the calcium content of the implant on day 12 in rats and is expressed as "bone forming units," where one bone forming unit represents the amount of protein that is needed for half maximal bone forming activity of the implant on day 12. Bone induction exhibited by intact demineralized rat bone matrix is considered to be the maximal bone differentiation activity for comparison purposes in this assay.

Cellular events during endochondral bone formation

Successful implants exhibit a controlled progression through the stages of protein-induced endochondral bone development, including: (1) transient infiltration by polymorphonuclear leukocytes on day one; (2) mesenchymal cell migration and proliferation on days two and three; (3) chondrocyte appearance on days five and six; (4) cartilage matrix formation on day seven; (5) cartilage calcification on day eight; (6) vascular invasion, appearance of osteoblasts, and formation of new bone on days nine and ten; (7) appearance of osteoclasts, bone remodeling and dissolution of the implanted matrix on days twelve to eighteen; and (8) hematopoietic bone marrow differentiation in the ossicles on day twenty-one. This time course in rats may be accelerated by increasing the amounts of OP-1 added. It is possible that increasing amounts of one or more MPSFs may also accelerate this time course. The shape of the new bone conforms to the shape of the implanted matrix.

Histological evaluation

Histological sectioning and staining is preferred to determine the extent of osteogenesis in the implants. Implants are fixed in Bouins Solution, embedded in paraffin, and cut into 6–8 μm sections. Staining with toluidine blue or hemotoxylin/eosin demonstrates clearly the ultimate development of endochondral bone. Twelve-day implants are usually sufficient to determine whether the implants contain newly-induced bone.

Biological markers

Alkaline phosphatase (AP)activity may be used as a marker for osteogenesis. The enzyme activity may be determined spectrophotometrically after homogenization of the implant. The activity peaks at 9–10 days in vivo and thereafter slowly declines. Implants showing no bone development by histology have little or no alkaline phosphatase activity under these assay conditions. The assay is useful for quantification and obtaining an estimate of bone formation quickly after the implants are removed from the rat. Alternatively, the amount of bone formation can be determined by measuring the calcium content of the implant.

Gene expression patterns that correlate with endochondral bone or other types of tissue formation can also be monitored by quantitating mRNA levels using procedures known to those of skill in the art such as Northern Blot analysis. Such developmental gene expression markers may be used to determine progression through tissue differentiation pathways after osteogenic protein/MPSF treatments. These markers include osteoblastic-related matrix proteins such as procollagen $\alpha_2$ (I), procollagen $\alpha_1$(I), procollagen $\alpha_1$(III), osteonectin, osteopontin, biglycan, and alkaline phosphatase for bone regeneration (see e.g., Suva et al., *J. Bone Miner.*

Res., 8, pp. 379–88 (1993); Benayahu et al., *J. Cell. Biochem.*, 56, pp. 62–73 (1994)).

EXAMPLE 8

Feline Model Bioassay for Bone Repair

A femoral osteotomy defect is surgically prepared. Without further intervention, the simulated fracture defect would consistently progress to non-union. The effects of osteogenic compositions and devices implanted into the created bone defects are evaluated by the following study protocol.

The 1 cm and 2 cm femoral defect cat studies demonstrate that devices comprising a matrix containing disposed osteogenic protein and MPSF can: (1) repair a weight-bearing bone defect in a large animal; (2) consistently induce bone formation shortly following (less than two weeks) implantation; and (3) induce bone by endochondral ossification, with a strength equal to normal bone, on a volume for volume basis. Furthermore, all animals remain healthy during the study and show no evidence of clinical or histological laboratory reaction to the implanted device. In this bone defect model, there is little or no healing at control bone implant sites. The results provide evidence for the successful use of the osteogenic compositions and devices of this invention to repair large, non-union bone defects.

Briefly, the procedure is as follows: Sixteen adult cats each weighing less than 10 lbs. undergo unilateral preparation of a 1 cm bone defect in the right femur through a lateral surgical approach. In other experiments, a 2 cm bone defect may be created. The femur is immediately internally fixed by lateral placement of an 8-hole plate to preserve the exact dimensions of the defect.

Three different types of materials may be implanted in the surgically created cat femoral defects: group I is a negative control group which undergoes the same plate fixation with implants of 4M guanidine-HCl-treated (inactivated) cat demineralized bone matrix powder (GuHCl-DBM) (360 mg); group II is a positive control group implanted with biologically active demineralized bone matrix powder (DBM) (360 mg); and groups III and IV undergo a procedure identical to groups I–II, with the addition of morphogenic protein alone (group III) and morphogenic protein+MPSF (group IV) onto each of the GuHCl-DBM carrier samples.

All animals are allowed to ambulate ad libitum within their cages post-operatively. All cats are injected with tetracycline (25 mg/kg subcutaneously (SQ) each week for four weeks) for bone labeling. All but four group III and four group IV animals are sacrificed four months after femoral osteotomy.

In vivo radiomorphometric studies are carried out immediately post-op at 4, 8, 12 and 16 weeks by taking a standardized X-ray of the lightly-anesthetized animal positioned in a cushioned X-ray jig designed to consistently produce a true anterio-posterior view of the femur and the osteotomy site. All X-rays are taken in exactly the same fashion and in exactly the same position on each animal. Bone repair is calculated as a function of mineralization by means of random point analysis. A final specimen radiographic study of the excised bone is taken in two planes after sacrifice.

At 16 weeks, the percentage of groups III and IV femurs that are united, and the average percent bone defect regeneration in groups I–IV are compared. The group I GuHCl-DMB negative-control implants should generally exhibit no bone growth at four weeks, less than 10% at eight and 12 weeks, and about 16% (+/−10%) at 16 weeks. The group II DMB positive-control implants should generally exhibit about 15–20% repair at four weeks, 35% at eight weeks, 50% (+/−10%) at 12 weeks and 70% (+/−12%) by 16 weeks.

Excised test and normal femurs may be immediately studied by bone densitometry, or wrapped in two layers of saline-soaked towels, placed into sealed plastic bags, and stored at −20° C. until further study. Bone repair strength, load-to-failure, and work-to-failure are tested by loading to failure on a specially designed steel 4-point bending jig attached to an Instron testing machine to quantitate bone strength, stiffness, energy absorbed and deformation to failure. The study of test femurs and normal femurs yields the bone strength (load) in pounds and work-to-failure in joules. Normal femurs exhibit a strength of 96 (+/−12) pounds. Osteogenic device-implanted femur strength should be corrected for surface area at the site of fracture (due to the "hourglass" shape of the bone defect repair). With this correction, the result should correlate closely with normal bone strength.

Following biomechanical testing, the bones are immediately sliced into two longitudinal sections at the defect site, weighed, and the volume measured. One-half is fixed for standard calcified bone histomorphometrics with fluorescent stain incorporation evaluation, and one-half is fixed for decalcified hemotoxylin/eosin stain histology preparation.

Selected specimens from the bone repair site are homogenized in cold 0.15 M NaCl, 3 mM $NaHCO_3$, pH 9.0 by a Spex freezer mill. The alkaline phosphatase activity of the supernatant and total calcium content of the acid soluble fraction of sediment are then determined.

EXAMPLE 9

Rabbit Model Bioassay for Bone Repair

This assay is described in detail in Oppermann et al., U.S. Pat. No. 5,354,557; see also Cook et al., J. of Bone and Joint Surgery, 76-A, pp. 827–38 (1994), which are incorporated herein by reference). Ulnar non-union defects of 1.5 cm are created in mature (less than 10 lbs) New Zealand White rabbits with epiphyseal closure documented by X-ray. The experiment may include implantation of devices into at least eight rabbits per group as follows: group I negative control implants of 4M guanidine-HCl-treated (inactivated) demineralized bone matrix powder (GuHCl-DBM); group II positive control implants with biologically active demineralized bone matrix powder (DBM); group III implants with osteogenic protein alone; group IV implants with osteogenic protein/MPSF combinations, and group V controls receiving no implant. Ulnae defects are followed for the full course of the eight week study in each group of rabbits.

In another experiment, the marrow cavity of the 1.5 cm ulnar defect is packed with activated osteogenic protein in rabbit bone powder in the presence or absence of a MPSF. The bones are allografted in an intercalary fashion. Negative control ulnae are not healed by eight weeks and reveal the classic "ivory" appearance. In distinct contrast, the osteogenic protein/MPSF-treated implants "disappear" radiographically by four weeks with the start of remineralization by six to eight weeks. These allografts heal at each end with mild proliferative bone formation by eight weeks. This type of device serves to accelerate allograft repair.

Implants treated with osteogenic protein in the presence of a MPSF may show accelerated repair, or may function at the same rate using lower concentrations of the osteogenic protein. As was described above, the rabbit model may also be used to test the efficacy of and to optimize conditions under which a particular osteogenic protein/MPSF combination can induce local bone and cartilage formation.

EXAMPLE 10

Dog Ulnar Defect Bioassay for Bone Repair

This assay is performed essentially as described in Cook et al., *Clinical Orthopaedics and Related Research*, 301, pp. 302–112 (1994), which is incorporated herein by reference). Briefly, an ulnar segmental defect model is used to evaluate bone healing in 35–45 kg adult male dogs. Experimental composites comprising 500 mg of insoluble bovine bone collagen are reconstituted with either 0, 625, 1200 or 2500 µg of OP-1 (preferably recombinant OP-1 expressed in CHO cells; Example 2B) in the absence or presence of increasing concentrations of one or more putative MPSFs. Any osteogenic protein may be used in place of OP-1 in this assay. Implantations at defect sites are performed with one carrier control and with the experimental series of OP-1 and OP-1/MPSF combinations being tested. mechanical testing is performed on ulnae of animals receiving composites at 12 weeks after implantation. Radiographs of the forelimbs are obtained weekly until the animals are sacrificed at either 12 or 16 postoperative weeks. Histological sections are analyzed from the defect site and from adjacent normal bone.

The presence of one or more MPSFs can increase the rate of bone repair in dog. The presence of one or more MPSFs may also permit the use of reduced concentrations of osteogenic protein per composite to achieve similar or the same results.

EXAMPLE 11

Monkey Ulnar and Tibial Defect Bioassay for Bone Repair

This bone healing assay in African green monkeys is performed essentially as described in Cook et al., *J. Bone and Joint Surgery*, 77A, pp. 734–50 (1995), which is incorporated herein by reference. Briefly, a 2.0 cm osteoperiosteal defect is created in the middle of the ulnar shaft and filled with an implant comprising various matrices containing 1000 µg of OP-1 (preferably recombinant OP-1 expressed in CHO cells; Example 2B) in the absence or presence of increasing concentrations of one or more putative MPSFs. Experimental composites comprising various matrices reconstituted with either 0, 250, 500 or 100 or 2000 µg of OP-1 in the absence or presence of increasing concentrations of one or more putative MPSFs were used to fill 2.0 cm osteoperiosteal defects created in the diaphysis of the tibia. Any osteogenic protein may be used in place of OP-1 in this assay. Implantations at defect sites are performed with one carrier control and with the experimental series of OP-1 and OP-1/MPSF combinations being tested. mechanical testing is performed on ulnae and tibia of animals receiving composites. Radiographs and histological sections are analyzed from the defect sites and from adjacent normal bone as described in Cook et al.

The presence of one or more MPSFs can increase the rate of bone repair in the monkey. The presence of one or more MPSFs may also permit the use of reduced concentrations of osteogenic protein per composite to achieve similar or the same results.

EXAMPLE 12

Rat Model Bioassay for Tendon/ligament-like Tissue Formation

The Sampath Reddi rat ectopic implant assay is modified such that the ethanol precipitation step is substituted with a dialysis step against water if the morphogenic protein/MPSF composition is a solution, or a diafiltering step against water if it is a suspension, followed by equilibration to 0.1% trifluoroacetic acid. The resulting solution is mixed with 20 mg of rat matrix, the mixture frozen, lyophilized and enclosed in #5 gelatin capsules (or other functionally equivalent devices). These devices are then implanted subcutaneously into abdominal thoracic region of rats (21–49 day old Male Long Evans rats were employed in Celeste et al.).

Subcutaneous implants are removed after ten days, and a section of each is processed using known procedures for histological analysis (see e.g., Ham and Cormack, *Histology* pp. 367–69 (J. B. Lippincott Co. 1979) (the disclosure of which is hereby incorporated by reference)). Glycolmethacrylate sections (1 µm) are stained with Von Kossa and acid fuschin to visualize and quantitate the amount of embryonic tendon/ligament-like tissue induced in each implant. Positive (e.g., containing BMP-12) and negative (e.g., a mock device) implant control groups are compared to experimental implants comprising either a morphogenic protein alone, or a morphogenic protein in combination with a MPSF. Embryonic tendon/ligament-like tissue, characterized by tightly-packed fibroblast bundles oriented in the same plane, can be observed in positive control implants after ten days.

EXAMPLE 13

Rat Model Bioassay for Nerve Regeneration and Repair

A matrix carrier is prepared. Wang et al. (WO 95/05846) used Collastat®, a collagen sponge (Vitaphore Wound Healing, Inc.), but any other desired carrier, such as those described herein, may be tested for applicability. The collagen carrier is prepared by washing, lyophilizing, sterilizing and degassing, and is then loaded with, for example, either: with no morphogenic protein (negative control group), with morphogenic protein only (group I), or with a particular combination of morphogenic protein/MPSF (group II). Variations on the experimental design allow one skilled in the art to test a variety of different morphogenic protein/MPSF combinations under various conditions.

All manipulations are performed under sterile conditions. The loaded matrices are placed inside approximately 1.6×20 mm lengths of sterile vented silastic or biodegradable tubing (stents) which may be trimmed to remove excess tubing before surgery. Vented silastic or biodegradable stents containing the matrices are applied microscopically and anastomized to the severed nerve endings, which are inserted into the stent for about 1 mm at each end, leaving a 15 mm "nerve defect" gap. Rats are tested for electrical return of function over a time course of weeks after implantation. Compound muscle action potentials (CMAPs) provide a reproducible transcutaneous measurement for assessing the degree of functional return. CMAP amplitude and latency is proportional to the number of reinnervated axon/motor endplates and thus serves as a useful index of neuronal regeneration.

Animals may be sacrificed for histopathological examination at various times post-implantation. Control stents implanted within subcutaneous tissues serve as histochemical controls.

What is claimed is:

1. A method for improving the tissue inductive activity of a morphogenic protein on a mammalian progenitor cell comprising the step of coadministering to the cell a morphogenic protein stimulatory factor (MPSF) selected from the group consisting of hormones, cytokines, peptides and growth factors, whereby the MPSF stimulates tissue induction by the morphogenic protein;

with the proviso that when the progenitor cell is an osteoblast stimulated to form bone and the morphogenic protein is activin, the MPSF may not be estrogen or calcitonin;

when the progenitor cell is an osteoblast stimulated to form bone and the morphogenic protein is a BMP homodimer or TGF-β, the MPSF may not be FGF, IGF-II, PDGF, estrogen, calcitonin or vitamin D;

when the progenitor cell is an osteoblast stimulated to form bone or cartilage and the morphogenic protein is a BMP homodimer, the MPSF may not be TGF-β; and when the progenitor cell is an osteoblast stimulated to form bone and the morphogenic protein is a homodimer of BMP-2 or BMP-3, the MPSF may not be parathyroid hormone.

2. The method according to claim 1, wherein the MPSF has an additive effect on stimulating tissue induction by the morphogenic protein.

3. The method according to claim 1, wherein the MPSF has a synergistic effect on stimulating tissue induction by the morphogenic protein.

4. The method according to claim 1, wherein the morphogenic protein is an osteogenic protein that is capable of inducing the progenitor cell to form endochondral or intramembranous bone.

5. The method according to claim 1, wherein the morphogenic protein is an osteogenic protein that is capable of inducing the progenitor cell to form cartilage.

6. The method according to claim 1, wherein the morphogenic protein is an osteogenic protein that is capable of inducing the progenitor cell to form tendon/ligament-like or neural tissue.

7. The method according to claim 1, wherein the morphogenic protein comprises a polypeptide selected from the group consisting of: BMP-2, BMP-4, BMP-5, BMP-6, OP-1 (BMP-7), BMP-8, BMP-9, BMP-10, BMP-11, BMP-12, and BMP-13, COP-5 and COP-7.

8. The method according to claim 1, wherein the morphogenic protein comprises a disulfide bonded dimeric species comprising a polypeptide selected from the group consisting of OP-1, BMP-2, BMP-4 and BMP-6.

9. The method according to claim 1, wherein the morphogenic protein comprises OP-1.

10. The method according to claim 1, wherein the morphogenic protein is produced by the expression of a recombinant DNA molecule in a host cell.

11. The method according to claim 1, wherein the morphogenic protein stimulatory factor comprises at least one compound selected from the group consisting of: insulin-like growth factor I (IGF-I), estradiol, growth hormone (GH), growth and differentiation factor (GDF), hydrocortisone (HC), insulin, progesterone, parathyroid hormone (PTH), vitamin D, retinoic acid and IL-6.

12. The method according to claim 1, wherein the MPSF is administered in an amount capable of synergistically stimulating the ability of the morphogenic protein to induce tissue formation in the mammal.

13. The method according to claim 1, wherein the morphogenic protein stimulatory factor comprises an agent that increases IGF-I bioactivity in the mammal.

14. The method according to claim 1, wherein the morphogenic protein is present at a concentration of at least about 1 ng/ml, and the morphogenic protein stimulatory factor is present at a concentration of at least about 0.01 ng/ml.

15. The method according to claim 1, wherein the morphogenic protein comprises OP-1 at a concentration of from about 1 ng/ml to about 500 ng/ml and the morphogenic protein stimulatory factor comprises IGF-I at a concentration from about 0.1 ng/ml to about 50 ng/ml.

16. The method according to claim 1, wherein the morphogenic protein comprises OP-1 at a concentration of from about 1 ng/ml to about 500 ng/ml and the morphogenic protein stimulatory factor comprises estradiol at a concentration of from about 0.05 nM to about 1000 nM.

17. The method according to claim 1, wherein the morphogenic protein comprises OP-1 at a concentration of from about 1 ng/ml to about 500 ng/ml and the morphogenic protein stimulatory factor comprises growth hormone at a concentration of from about 5 ng/ml to about 1000 ng/ml.

18. The method according to claim 1, wherein the morphogenic protein comprises OP-1 at a concentration of from about 1 ng/ml to about 500 ng/ml and the morphogenic protein stimulatory factor comprises hydrocortisone at a concentration of from about 0.05 nM to about 5.0 nM.

19. The method according to claim 1, wherein the morphogenic protein comprises OP-1 at a concentration of from about 1 ng/ml to about 500 ng/ml and the morphogenic protein stimulatory factor comprises insulin at a concentration of from about 0.01 nM to about 1000 nM.

20. The method according to claim 1, wherein the morphogenic protein comprises OP-1 at a concentration of from about 1 ng/ml to about 500 ng/ml and the morphogenic protein stimulatory factor comprises parathyroid hormone at a concentration of from about 10 nM to about 1000 nM.

21. The method according to claim 1, wherein the morphogenic protein comprises OP-1 at a concentration of from about 1 ng/ml to about 500 ng/ml and the morphogenic protein stimulatory factor comprises progesterone at a concentration of from about 0.05 nM to about 1000 nM.

* * * * *